US012697239B2

(12) United States Patent
Loganathan et al.

(10) Patent No.: US 12,697,239 B2
(45) Date of Patent: Aug. 4, 2026

(54) IMPLANT DELIVERY SYSTEM AND METHOD OF USE

(71) Applicants: STRYKER CORPORATION, Kalamazoo, MI (US); STRYKER EUROPEAN OPERATIONS LIMITED, Carrigtwohill (IE)

(72) Inventors: Siddharth Loganathan, Santa Clara, CA (US); Beth Oldford, Kalamazoo, MI (US); Jeffrey Lu, Kalamazoo, MI (US); Rajan Chandrasekaran, Kalamazoo, MI (US)

(73) Assignees: Stryker Corporation, Kalamazoo, MI (US); Stryker European Operations Limited, Carrigtwohill (IE)

( * ) Notice: Subject to any disclaimer, the term of this patent is extended or adjusted under 35 U.S.C. 154(b) by 389 days.

(21) Appl. No.: 18/539,101

(22) Filed: Dec. 13, 2023

(65) Prior Publication Data

US 2024/0130880 A1 Apr. 25, 2024

Related U.S. Application Data

(63) Continuation of application No. PCT/US2022/030267, filed on May 20, 2022.

(Continued)

(51) Int. Cl.
| | |
|---|---|
| *A61F 2/966* | (2013.01) |
| *A61B 90/00* | (2016.01) |
| *A61M 25/01* | (2006.01) |

(52) U.S. Cl.
CPC ...... *A61F 2/966* (2013.01); *A61B 2090/3966* (2016.02); *A61F 2250/0098* (2013.01); *A61M 25/0108* (2013.01)

(58) Field of Classification Search
CPC ............ A61F 2/966; A61F 2250/0098; A61M 25/0108; A61B 2090/3966
See application file for complete search history.

(56) References Cited

U.S. PATENT DOCUMENTS

| | | |
|---|---|---|
| 2004/0133232 A1 | 7/2004 | Rosenbluth et al. |
| 2008/0051870 A1* | 2/2008 | Kaufmann ............. A61B 90/39 623/1.34 |

(Continued)

FOREIGN PATENT DOCUMENTS

| | | |
|---|---|---|
| CA | 2721902 C | 7/2017 |
| JP | 2012-187177 A | 10/2012 |

(Continued)

OTHER PUBLICATIONS

Foreign Exam Report for EP Patent Appln. No. 22 731 383.0 dated May 2, 2024.

(Continued)

*Primary Examiner* — Javier G Blanco
(74) *Attorney, Agent, or Firm* — Vista IP Law Group, LLP

(57) ABSTRACT

Methods and systems for delivering a tubular implant to a target location in a body lumen, wherein the tubular implant has a delivery length when in a radially collapsed, delivery configuration, and a foreshortened length shorter than the delivery length when in a radially expanded, implanted configuration. Respective markers are provided on a delivery catheter and on the tubular implant which provide a visual indication of the landing location of a foreshortened length of a last proximal portion of the tubular implant prior to implanting the last proximal portion. This allows the clinician to determine if the landing location of the last proximal portion is clinically desirable prior to fully implanting the tubular implant.

12 Claims, 11 Drawing Sheets

Related U.S. Application Data

(60) Provisional application No. 63/210,410, filed on Jun. 14, 2021.

(56) References Cited

U.S. PATENT DOCUMENTS

| | | |
|---|---|---|
| 2012/0172963 A1 | 7/2012 | Ryan et al. |
| 2018/0344493 A1 | 12/2018 | Epstein |

FOREIGN PATENT DOCUMENTS

| | | |
|---|---|---|
| WO | WO 2014/042900 A1 | 3/2014 |
| WO | WO 2015/167997 A1 | 11/2015 |
| WO | WO 2022/265810 | 12/2022 |

OTHER PUBLICATIONS

Foreign Exam Report for EP Patent Appln. No. 22 731 383.0 dated Apr. 2, 2025.

PCT International Search Report for PCT/US2022/030267, Applicant: Stryker Corporation et al., Form PCT/ISA/210 and 220, dated Sep. 12, 2022 (6 pages).

PCT Written Opinion of the International Search Authority for PCT/US2022/030267, Applicant: Stryker Corporation et al., Form PCT/ISA/237, dated Sep. 12, 2022 (10 pages).

Foreign Communication EP Patent Appln. No. 22 731 383.0 dated Oct. 16, 2024.

Foreign OA for JP Patent Appln. No. 2023-573572 dated Mar. 17, 2026 (with English translation).

Foreign Exam Report for IN Patent Appln. No. 202347087039 dated May 8, 2026.

* cited by examiner

IMPLANT DELIVERY SYSTEM AND METHOD OF USE

RELATED APPLICATION DATA

This application is a continuation of International Patent Application No. PCT/US2022/030267, filed on May 20, 2022, which claims priority to U.S. Provisional Patent Application No. 63/210,410, filed Jun. 14, 2022, the disclosures of all of which are hereby incorporated herein by reference in their entirety into the present application.

FIELD

The present disclosure pertains generally to systems and methods for delivering medical implants. More particularly, the present disclosure pertains to delivery systems and methods for delivering a tubular implant to a target site in a vasculature of a patient.

BACKGROUND

The use of intravascular medical devices and implants has become an effective method for treating many types of vascular disease. In general, a suitable intravascular device is inserted into the vascular system of the patient and navigated through the vasculature to a target site in a patient. Using this method, virtually any target site in the patient's vascular system may be accessed, including the coronary, cerebral, and peripheral vasculature.

Catheters are often utilized to place medical implants, such as stents and embolic devices, at a desired location within a body. Usually, stents are tubular prosthesis for insertion through body lumens; although, stents may have a wide variety of sizes and shapes. A stent may be delivered by being mounted over a balloon and loaded onto a catheter, and after positioning the stent at the desired location, the balloon is inflated to expand the stent radially outward. Alternatively, a stent may be loaded onto a catheter in a reduced configuration and/or diameter; then the catheter is withdrawn from the stent thereby introducing the stent into the lumen of a body vessel. For example, self-expanding stents are to be delivered in an elastically compressed or collapsed state while being confined within a tubular restraining member, such as a catheter. The catheter is advanced through the vascular system until its distal end reaches the implantation site. Additionally, the catheter may be introduced into the patient over a guidewire which has been previously introduced, in the so-called "over-the-wire" and "rapid-exchange" delivery systems. The collapsed stent is typically mounted on a pusher member or a delivery wire, disposed within the lumen of the catheter, so that the stent is introduced, and advanced or pushed through the catheter. When the stent is positioned adjacent to the desired location, it is unsheathed by withdrawing the catheter relative to the stent, and allowing the stent to expand to a predetermined diameter in the body vessel, thereby engaging the interior walls of the vessel, without requiring assistance from a balloon.

A self-expanding stent may be biased so as to expand upon release from the delivery catheter and/or it may include a shape-memory component which allows the stent to expand upon exposure to a predetermined condition. Some stents may be characterized as hybrid stents which have some characteristics of both self-expandable and balloon expandable stents. In either configuration, once delivered to a target location within the body, the expanded stent supports and reinforces the vessel wall while maintaining the vessel in an open and unobstructed condition.

In some medical applications, such as bridging the neck of an aneurysm, or diverting blood flow from an aneurysm or a blood vessel, an accurate implantation of a self-expanding stent or tubular implant in a target location is needed. Some implant delivery systems include a radio-opaque marker at the distal end tip of delivery catheters, so physicians may estimate a distal landing of the tubular implant when the stent is delivered out of the distal end tip of the delivery catheter, with the assistance of fluoroscopic imaging systems. However, when confined within a delivery catheter, a collapsed self-expanding stent or tubular implant usually has a larger delivery length than its implanted length, when the stent or tubular implant is expanded in an implanted configuration, making it difficult for the physicians to estimate a proximal landing of the proximal end of the implanted stent or tubular implant. Thus, there may be an increased risk of failure and duration of the medical procedure, or at least, a failure to deliver the stent or tubular implant in a target location, for example, to accurately bridge the neck of the aneurysm or divert the blood flow out of a blood vessel, as desired. Accordingly, there is an ongoing need to provide a delivery system for delivering self-expanding tubular implants that provides more accurate delivery and positioning of the implant at a target location.

SUMMARY

In one embodiment of the disclosed inventions, a method of delivering a tubular implant to a target location in a body lumen is provided, wherein the tubular implant has a delivery length when in a radially collapsed, delivery configuration, and a foreshortened length shorter than the delivery length when in a radially expanded, implanted configuration. In other words, the radially collapsed tubular implant decreases in length as it radially expands, a characteristic commonly known as foreshortening. The amount of foreshortening of the tubular implant depends on the amount of radial expansion of the tubular implant, which in turn depends on the diameter (or other lateral dimension) of the body lumen in which the tubular implant expands. For example, in a smaller diameter body lumen, the tubular implant radially expands a smaller amount than in a larger diameter body lumen, and the tubular implant foreshortens a smaller amount than in a larger diameter body lumen. In many cases, the diameter of the body lumen varies along the length of the implanted tubular member, in which case the amount of foreshortening of portions of the tubular implant will vary along the length of the implanted tubular member. For instance, where a distal portion of the landing location in a body lumen has a large diameter, and a proximal portion of the landing location in the body lumen has a smaller diameter, the distal portion of the tubular member located will foreshorten more than the proximal portion of the tubular member.

The varying amount of foreshortening of the tubular implant based on the diameter of the body lumen present several problems, and the varying diameter of the body lumen. For one, it is very difficult to accurately determine the full, foreshortened length of the tubular implant in its expanded, implanted configuration because of the varying diameter of the body lumen. Determining the full foreshortened length of the tubular implant in its expanded, implanted configuration requires accurately determining the cross-section of the body lumen along the entire implanted length of the tubular implant, and then determining how much foreshortening will occur at each portion of the tubular implant along the cross-section of the entire implanted length. Furthermore, even if this determination can be made, as the tubular implant is positioned and delivered from a delivery catheter, there can be variations in the position of the tubular implant and the cross-section of the body lumen from the original determination of the cross-section used to determine the full, implanted length. Hence, once the implant is fully, or substantially fully, released from the delivery catheter into the body lumen, a physician may find that the location of the last proximal portion of the tubular implant is displaced from a target proximal landing location of the proximal end of the tubular implant. For instance, the physician may use a fluoroscopic imaging system to visualize the implantation and find that the location of the proximal portion of the tubular implant is clinically undesirable. The position may be clinically undesirable for a number of reasons, such as the proximal portion failing to cover an entire aneurysm being treated, or the proximal portion lands on a bend which could causes a thrombosis or stroke, or the proximal portion covers another vessel. In this case, the physician may need to re-position the stent. However, it can be very difficult to re-position the stent once it has been fully, or almost fully implanted. For example, the delivery catheter may be removed from the stent past a point-of-no-return in which the tubular member cannot be re-sheathed into the delivery catheter. This significantly complicates the process of re-positioning the stent, if the stent can be re-positioned at all.

The present invention is directed to an improved implant delivery system and method of use which allows a more accurate determination of a landing location of a last proximal portion of a tubular implant. The improved implant delivery system and method for implanting a foreshortening tubular implant uses specially placed markers to indicate when a determined deployed length (i.e., the foreshortened length) of a last proximal portion of the tubular implant is still remaining to be deployed from a delivery catheter. As a non-limiting example, a tubular implant may have a full delivery length in its radially collapsed, delivery configuration of 120 mm. The length of the determined deployed length is determined based upon the cross-section of the body lumen at the target proximal landing location for the proximal portion of the tubular implant. As an example, the cross-section may be measured using any suitable technique, such as visualization, estimates based on type of body lumen and location in the body, etc. The determined deployed length can then be calculated based on the characteristics of the tubular implant and the cross-section of the body lumen. As one example, a last proximal portion may be 9.5 mm in the radially collapsed, delivery configuration, and have a determined deployed length in the target proximal landing location of 5 mm. As described in more detail below, the markers are located on the device to indicate when the delivery catheter has been withdrawn to the point that there is the determined deployed length (in the example, 5 mm) remaining to be deployed from the delivery catheter. In other words, there is 9.5 mm of tubular implant in the radially collapsed, delivery configuration remaining in the delivery catheter. In this way, the physician can identify (such as by visualization) where the last 5 mm of implanted tubular implant will land in the body lumen. Because the improved system and method determines a length of only a shorter proximal portion of the tubular implant, the determination of the position of the last proximal portion is much more accurate than for prior systems and methods. This reduces or even eliminates the effects of vessel tapering, aneurysm neck length, implant loading, and other factors which cause inaccuracies in the determination of the full length of a foreshortening tubular implant.

Accordingly, one embodiment of the present invention is directed to a method for delivering a tubular implant to a target location in a body lumen. The tubular implant has a delivery length when in a radially collapsed, delivery configuration, and a foreshortened length shorter than the delivery length when in a radially expanded, implanted configuration. The implant delivery system comprises the tubular implant disposed in the collapsed, delivery configuration within a delivery catheter. The implant delivery system is inserted into the body lumen and advanced until a distal end of the tubular implant is adjacent a target distal landing location for the distal end of the tubular implant.

The delivery catheter is then withdrawn to deliver the tubular implant into the body lumen. The delivery catheter is withdrawn until a first marker disposed on a distal end of the delivery catheter reaches a second marker located on the implant delivery system. For instance, the first marker may be disposed on the distal end of the delivery catheter, and the second marker may be disposed on the implant delivery system (for example, on the tubular implant or a delivery wire) such that the first marker moves relative to the second marker as the delivery catheter is withdrawn. In certain embodiments, the first marker may be a single, small radiopaque marker. In other embodiments, the first marker may be an elongated radiopaque marker and a radiopaque coil.

The first and second markers are respectively positioned such that when the first marker reaches the second mark, there is a last proximal portion of the tubular implant remaining to be deployed from the delivery catheter. The last proximal portion has a determined deployed length which is a foreshortened length of the last proximal portion in its radially expanded configuration corresponding to a determined cross-section of the body lumen at a target proximal landing location for the proximal portion of the tubular implant. In other words, the first and second marker indicate when there is a known foreshortened length of tubular implant remaining to be deployed into the body lumen based on the amount of radial expansion of the last proximal portion in the cross-section of the target proximal landing location for the last proximal portion.

The foreshortened length of the last proximal portion may be determined in various ways. As one example, the cross-section of the proximal landing location of the body lumen can be measured, using any suitable means, such as by imaging, gauges, etc. The cross-section can be average value, a varying profile, or other suitable measurement. Then, the foreshortened length of the last proximal portion in its radially expanded configuration can be calculated or determined based on the determined cross-section.

In another aspect of the method, the implant delivery system may also include a re-sheath marker disposed on the implant delivery system. The re-sheath marker is positioned such that when the delivery catheter is withdrawn to the point that the first marker reaches the re-sheath marker, the re-sheath marker indicates a position of the proximally withdrawn delivery catheter at which the catheter cannot be advanced distally to re-sheath the tubular implant into the delivery catheter.

In still another aspect of the method, the second marker may be located distally from the re-sheath marker along the implant delivery system. This ensures that the delivery catheter can be withdrawn to deploy the tubular implant up to the last proximal portion of the tubular implant, such that there is a known deployed length remaining, and the tubular member can still be re-sheathed by advancing the delivery catheter distally over the tubular member. This allows a physician to determine whether the landing location of the last proximal portion is clinically desirable, and if not, to re-sheath and re-position the implant delivery system within the body lumen.

In yet another aspect, the method may further include determining a cross-section of the body lumen at the target proximal landing location, and then locating the second marker longitudinally along the implant delivery system based on the determined cross-section to provide for the predetermined deployed length. In this case, the position of the second marker is adjustable to adjust and set the determined deployed length of the last proximal portion of the tubular implant.

In another aspect, the method further includes identifying a position of the first marker within the body lumen at the point at which delivery catheter is withdrawn such that the first marker reaches the second marker; and determining, based on the identified position of the first marker and the predetermined deployed length of a proximal portion of the tubular implant remaining to be deployed from the delivery catheter, whether a proximal landing location of the proximal portion of the tubular implant is clinically desirable.

In still another aspect, the method may further comprise determining, based on the identified position of the first marker and the predetermined deployed length of a proximal portion of the tubular implant remaining to be deployed from the delivery catheter, that the proximal landing location of the proximal portion of the tubular implant is clinically undesirable. Then, advancing the delivery catheter distally to fully re-sheath the tubular implant within the delivery catheter. In still another aspect, the implant delivery system may be re-positioned to a new location with tubular implant fully re-sheathed within delivery catheter. Once re-positioned to the new location, the described procedures for deploying the tubular implant, determining whether the proximal landing location is clinically desirable, re-sheathing the tubular implant, and/or re-positioning the implant delivery system, may be repeated as many times as needed to deploy the tubular implant in a clinically desirable location.

In another aspect of the method, the implant delivery system may further include a delivery wire (e.g. a pusher wire) slidably disposed in the delivery catheter. The tubular implant may be mounted on the delivery wire for deployment out of the open end of the delivery catheter into the body lumen when the delivery catheter is withdrawn proximally relative to the delivery wire. In another aspect, the second marker may be mounted on the delivery wire.

In additional aspects of the method, the tubular implant may comprise one of a stent or a blood flow diverter.

In still another aspect, the tubular implant may be self-expanding. Alternatively, the tubular implant may be expanded by a balloon system disposed on the implant delivery system.

In accordance with another embodiment of the disclosed inventions, an implant delivery system for implanting a tubular implant in a body lumen is provided. The system includes a delivery catheter comprising an elongated tubular member having a lumen, a proximal end and open distal end. A first marker is disposed on the distal end of the delivery catheter. A tubular implant is disposed within the lumen of the tubular member. The tubular implant has a delivery length when in a collapsed, delivery configuration within the delivery catheter, and a foreshortened length in a radially expanded, implanted configuration when released out of the delivery catheter.

A delivery wire is slidably disposed in the delivery catheter, and the tubular implant is detachably coupled to the delivery wire for delivery through and out the open end of the delivery catheter. A second marker is located on one of the delivery wire or the tubular implant. The second marker is positioned such that a last proximal portion of the tubular implant extending from the position of the second marker to a proximal end of the tubular implant has a determined deployed length in its radially expanded and foreshortened configuration corresponding to a determined cross-section of the body lumen at a target proximal landing location for the last proximal portion of the tubular implant. Same as the method described above, the first and second marker indicate when there is a known foreshortened length of tubular implant remaining to be deployed into the body lumen based on the amount of radial expansion of the last proximal portion in the cross-section of the target proximal landing location for the last proximal portion.

In another aspect, the implant delivery system may further comprise a re-sheath marker disposed on the implant delivery system such that the first marker moves along with the delivery sheath relative to the re-sheath marker upon withdrawing the delivery sheath from the tubular implant. The re-sheath marker is positioned such that when the delivery catheter is withdrawn to the point that the first marker reaches the re-sheath marker, the re-sheath marker indicates a position of the proximally withdrawn delivery catheter at which the catheter cannot be advanced distally to re-sheath the tubular implant into the delivery catheter.

In still another aspect, the second marker may be located distally from the re-sheath marker along the implant delivery system. This ensures that the delivery catheter can be withdrawn to deploy the tubular implant up to the last proximal portion of the tubular implant, such that there is a known deployed length remaining, and the tubular member can still be re-sheathed by advancing the delivery catheter distally over the tubular member. This allows a physician to determine whether the landing location of the last proximal portion is clinically desirable, and if not, to re-sheathe and re-position the implant delivery system within the body lumen.

In another aspect, the second marker may be located longitudinally along the implant delivery system based on a determined cross-section of the body lumen at the target proximal landing location to provide for the determined deployed length of the proximal portion of the tubular implant.

In yet another aspect, the determined cross-section of the body lumen at the target proximal landing location may be an average diameter of the body lumen along a portion of the body lumen at the target proximal landing location. The cross-section can be an average value, a varying profile, or other suitable measurement of the body lumen. Then, the foreshortened length of the last proximal portion in its radially expanded configuration is be calculated or determined based on the determined cross-section. In another aspect, the determined cross-section of the body lumen at the target proximal landing location may be based on a measurement of a cross-section of the body lumen at the target proximal landing location. For example, the cross-section of the proximal landing location of the body lumen can be measured, using any suitable means, such as by imaging, gauges, etc. In an alternative aspect, the determined cross-section of the body lumen at the target proximal landing location may be based on an approximation using a standard cross-section of a body lumen.

In still another aspect, the second marker may be adjustably locatable on the delivery wire or the tubular implant such that the second marker can be adjusted to set the determined deployed length of the last proximal portion.

In yet another aspect, the second marker may be mounted on the delivery wire. In an alternative aspect, the second marker may be disposed on the tubular implant.

In still another aspect, the tubular implant may be a stent or a blood flow diverter. In still another aspect of the system, the tubular implant may be self-expanding. Alternatively, the tubular implant may be expanded by a balloon system disposed on the implant delivery system.

Another embodiment of the present invention is directed to a system and method in which a set of implant delivery systems for implanting a tubular implant is made available in which each delivery system is configured for a different cross-section of the proximal landing location in the body lumen. The clinician may then determine the cross-section of the proximal landing location, and then select an implant delivery system configured for that cross-section. Accordingly, a selection of implant delivery systems comprising a plurality of delivery systems is made available in which each of the respective delivery systems is configured for a different cross-section (i.e., cross-section diameter) of the proximal landing location of the body lumen. The axial position of a proximal portion marker is set on each respective delivery system to provide a predetermined deployed length of the last proximal portion for a given cross-section of proximal landing location of the body lumen. For example, a set of implant delivery systems may be configured to provide a consistent predetermined deployed length (e.g., 5 mm) for various different cross-sections (e.g., 3.0 mm, 3.5 mm, 4.0 mm, 4.5 mm, 5.0 mm, etc.).

A method of selecting and using an implant delivery system from the set of a plurality of implant delivery systems is as follows. First, the cross-section of the proximal landing location of the body lumen is determined. Then, the clinician selects an appropriate one of the implant delivery systems from the set which best corresponds to the determined cross-section. Then, the selected implant delivery system is used according to the same methods described above.

Still another embodiment of the present invention is directed to a medical assembly for implanting a tubular implant in which the tubular implant is configured to be used for a range of cross-sections of a proximal landing location of a body lumen. The medical assembly is very similar to the medical assembly described above, except that it includes a delivery system which has a tubular implant having two proximal portion markers, a first proximal portion marker and a second proximal portion marker, instead of a single proximal portion marker. The two proximal portion markers are axially positioned to provide a predetermined deployed length for a range of cross-sections of the proximal landing location of the body lumen. The first proximal portion marker and second proximal portion marker 55*b* may have different shapes or different radiopaque indications to visually distinguish the markers from each other. The first proximal portion marker and second proximal marker are positioned at different axial locations on the tubular implant, such as the first proximal portion marker being positioned axially distal of the second proximal marker. As an example, the first proximal portion marker may provide a predetermined deployed length (e.g., 5.0 mm) in a first cross-section of the proximal landing location (e.g., 4.0 mm), and the second proximal portion marker may provide the predetermined deployed length (e.g., 5.0 mm) in a second cross-section less than the first cross-section (e.g., 3.5 mm). Hence, delivery system provides a nominal predetermined deployed length (e.g., 5.0 mm) for the range from the first cross-section to the second cross-section (e.g., from 3.5 mm to 4.0 mm)

In still another embodiment, a selection of implant delivery systems for a range of cross-section may be provided similar to the selection of implant delivery systems, described above. Each of the delivery systems in the set of a plurality of delivery systems is configured for a different range of cross-sections (i.e., range of cross-section diameters) of the proximal landing location of the body lumen. In this way, the axial positions of the two proximal portion markers are set on each respective delivery system to provide a predetermined deployed length for a given range of cross-sections of proximal landing location of the body lumen. For instance, a set of implant delivery systems may be configured to provide a predetermined deployed length (e.g., 5 mm) for various different ranges of cross-sections, such as for cross-section diameters of 3.0-3.5 mm, 3.5-4.0 mm, 4.0-4.5 mm, 4.5-5.0 mm, 5.0-5.5 mm, etc.

A method of selecting and using an implant delivery system 102 from the set of a plurality of ranged implant delivery system is as follows. First, the cross-section of the proximal landing location of the body lumen is determined. Then, the clinician selects one of the ranged implant delivery systems from the set having a range which includes or encompasses the determined cross-section. Then, the selected ranged implant delivery system according to the same methods described above.

The following are additional embodiments disclosed herein:

1. An implant delivery system for implanting a tubular implant in a body lumen, comprising:
   a delivery catheter comprising an elongated tubular member having a lumen, a proximal end and open distal end;
   a first marker disposed on the distal end of the delivery catheter;
   a tubular implant disposed within the lumen of the tubular member, the tubular implant having a delivery length when in a collapsed, delivery configuration within the delivery catheter, and a foreshortened length in a radially expanded, implanted configuration when released out of the delivery catheter;
   a pusher member slidably disposed in the delivery catheter, wherein the tubular implant is detachably coupled to the pusher member for delivery through and out the open end of the delivery catheter; and
   a second marker located on one of the pusher member and tubular implant, the second marker positioned such that a last proximal portion of the tubular implant extending from the position of the second marker to a proximal end of the tubular implant has a determined deployed length in its radially expanded and foreshortened configuration corresponding to a determined cross-section of the body lumen at a target proximal landing location for the last proximal portion of the tubular implant.

2. The implant delivery system of 1 above, further comprising
   a re-sheath marker disposed on the implant delivery system such that the first marker moves along with the delivery sheath relative to the re-sheath marker upon withdrawing the delivery sheath from the tubular implant, the re-sheath marker indicating a proximal most position to which the first marker can be withdrawn beyond which the delivery catheter cannot be advanced distally to re-sheath the tubular implant into the delivery catheter.

3. The implant delivery system of 2 above, wherein the second marker is located distally from the re-sheath marker along the implant delivery system.

4. The implant delivery system of any of 1-3 above, wherein the second marker is located longitudinally along the implant delivery system based on a determined cross-section of the body lumen at the target proximal landing location to provide for the determined deployed length of the proximal portion of the tubular implant.

5. The implant delivery system of any of 1-3 above, wherein the second marker is adjustably locatable on the pusher member or the tubular implant such that the second marker can be adjusted to set the determined deployed length of the last proximal portion.

6. The implant delivery system of any of 1-3 above, wherein the second marker is mounted on the pusher member.

7. The implant delivery system of any of 1-3 above, wherein the second marker is disposed on the tubular implant.

8. The implant delivery system of any of 1-7 above, wherein the tubular implant comprises a stent or a flow diverter.

9. The implant delivery system of any of 1-8 above, wherein the tubular implant is self-expanding.

10. The implant delivery system of any of 1-9 above, wherein the determined cross-section of the body lumen at the target proximal landing location comprises an average diameter of the body lumen along a portion of the body lumen at the target proximal landing location.

11. The implant delivery system of any of 1-9 above, wherein the determined cross-section of the body lumen at the target proximal landing location is based on a measurement of a cross-section of the body lumen at the target proximal landing location.

12. The implant delivery system of any of 1-9 above, wherein the determined cross-section of the body lumen at the target proximal landing location is based on an approximation using a standard cross-section of a body lumen.

13. The implant delivery system of any of 1-9 above, wherein the determined cross-section of the body lumen at the target proximal location.

14. A method for delivering a tubular implant to a target location in a body lumen, the tubular implant having a delivery length when in a radially collapsed, delivery configuration, and a foreshortened length shorter than the delivery length when in a radially expanded, implanted configuration, the method comprising:

inserting an implant delivery system comprising the tubular implant disposed in the collapsed, delivery configuration within a delivery catheter into the body lumen and advancing the implant delivery system until a distal end of the tubular implant is adjacent a target distal landing location for the distal end of the tubular implant; and withdrawing the catheter until a first marker disposed on a distal end of the delivery catheter reaches a second marker located on the implant delivery system at which point there is a last proximal portion of the tubular implant remaining to be deployed from the delivery catheter, wherein the last proximal portion has a determined deployed length, the determined deployed length being a foreshortened length of the proximal portion in its radially expanded configuration corresponding to a determined cross-section of the body lumen at a target proximal landing location for the proximal portion of the tubular implant.

15. The method of 14 above, wherein the implant delivery system further comprises a re-sheath marker disposed on the implant delivery system, wherein when the delivery catheter is withdrawn to the point that the first marker reaches the re-sheath marker, the re-sheath marker indicates a position of the proximally withdrawn delivery catheter at which the catheter cannot be advanced distally to re-sheath the tubular implant into the delivery catheter.

16. The method of 15 above, wherein the second marker is located distally from the re-sheath marker along the implant delivery system.

17. The method of 14 above, further comprising:

determining a cross-section of the body lumen at the target proximal landing location; and locating the first marker longitudinally along the implant delivery system based on the determined cross-section to provide for the determined deployed length.

18. The method of 17 above, wherein determining a cross-section of the body lumen at the target proximal landing location comprises determining an average diameter of the body lumen along a portion of the body lumen at the target proximal landing location.

19. The method of 14 above, further comprising:

determining a cross-section of the body lumen at the target proximal landing location; and determining the predetermined deployed length based on the determined cross-section.

20. The method of 19 above, wherein determining a cross-section of the body lumen at the target proximal landing location comprises determining an average diameter of the body lumen along a portion of the body lumen at the target proximal landing location.

21. The method of 14 above, further comprising identifying a position of the first marker within the body lumen at the point at which the delivery catheter is withdrawn such that the first marker reaches the second marker; and determining, based on the identified position of the first marker and the predetermined deployed length of the last proximal portion of the tubular implant remaining to be deployed from the delivery catheter, whether a proximal landing location of the proximal portion of the tubular implant is clinically desirable.

22. The method of 14 above, further comprising identifying a position of the first marker within the body lumen at the point at which delivery catheter is withdrawn such that the first marker reaches the second marker;

determining, based on the identified position of the first marker and the predetermined deployed length of a proximal portion of the tubular implant remaining to be deployed from the delivery catheter, a proximal landing location of the proximal portion of the tubular implant is clinically undesirable; and advancing the delivery catheter distally to fully re-sheath the tubular implant within the delivery catheter.

23. The method of 22 above, further comprising repositioning the implant delivery system with tubular implant fully re-sheathed within delivery catheter to a new location.

24. The method of 23 above, further comprising with the implant delivery system in the new location, withdrawing the catheter until the first marker on the delivery catheter reaches the second marker located on the implant delivery system;

identifying a position of the first marker within the body lumen at the point at which delivery catheter is withdrawn such that the first marker reaches the second marker; and determining, based on the identified position of the first marker and the predetermined deployed length of a proximal portion of the tubular implant remaining to be deployed from the delivery catheter, whether a proximal landing location of the proximal portion of the tubular implant is clinically desirable.

25. The method of 14 above, wherein the implant delivery system further comprises a pusher member slidably disposed in the delivery catheter, wherein the tubular implant is detachably coupled to the pusher member for delivery out of an open end of the delivery catheter into the body lumen when the delivery catheter is withdrawn proximally relative to the pusher member.

26. The method of 25 above, wherein the second marker is mounted on the pusher member.

27. The method of 14 above, wherein the second marker is disposed on the tubular implant.

28. The method of 14 above, wherein the tubular implant comprises a stent or a flow diverter.

29. The method of 28 above, wherein the tubular implant is self-expanding.

DETAILED DESCRIPTION

Figure 1:
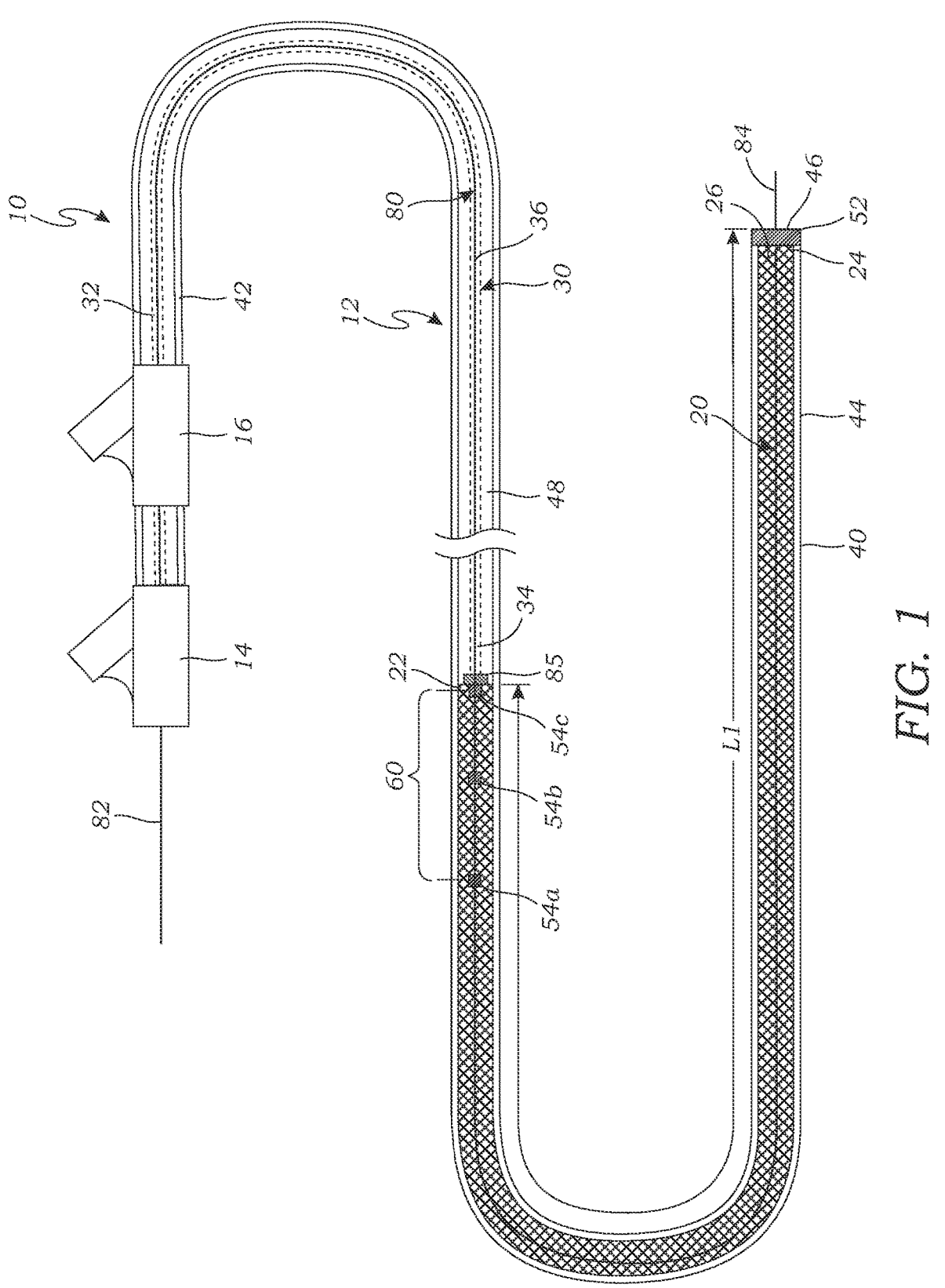
FIG. 1 is a side view of a medical assembly including an implant delivery system for delivering a tubular implant, according to one embodiment of the disclosed inventions.

For the following defined terms, these definitions shall apply, unless a different definition is set forth in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5). As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

Referring to FIG. 1 a side view of a medical assembly 10 for delivering an expandable tubular implant 20 into a target site of a patient is shown, according to one embodiment of the disclosed inventions. The medical assembly 10 includes a delivery system 12 having a tubular implant 20, such as a stent or a flow diverter, detachably coupled to the implant delivery system 12. The delivery system 12 and tubular implant may be composed of suitable polymeric materials, metals and/or alloys, such as polyethylene, stainless steel or other suitable biocompatible materials or combinations thereof.

The delivery system 12 is dimensioned to reach remote locations of a vasculature and is configured to deliver the tubular implant 20 to a target location in a patient's body, such as an occlusion in a blood vessel, in a blood vessel adjacent to an aneurysm neck, a bifurcated blood vessel, or the like. The delivery system 12 includes a delivery configuration in which the tubular implant 20 is in a radially constrained and collapsed configuration, having a full delivery length L1 (see FIGS. 1, 3A-B). The delivery system 12 further includes a deployed configuration in which the tubular implant 20 is expanded into a deployed configuration when deployed out of the delivery system 12, having a full implanted length L2 (FIGS. 2, 3A) that is shorter than the delivery length L1, which will be described in more detail below.

The tubular implant 20 includes a tubular resilient member having a proximal end 22, a distal end 24, and defining an inner lumen 26 extending therebetween. The tubular implant 20 is biased to expand from a constrained delivery configuration with the delivery catheter 40, to a radially expanded, implanted configuration when released out of the delivery catheter 40. Upon expanding to the radially expanded, implanted configuration, the tubular member 20 foreshortens. In other words, when the tubular implant 20 is constrained within the catheter 40 in the radially constrained and collapsed configuration, the delivery length L1 (FIGS. 1, 3A-B) of the tubular implant 20 is longer than the implanted length L2 (FIGS. 2, 3A). The tubular implant 20 is biased to extend radially outwards upon release from the delivery system 12.

The tubular implant 20 may be constructed from a variety of materials such as stainless steel, elgiloy, nickel, titanium, nitinol, shape memory polymers, or combinations thereof. The tubular implant 20 may also be formed in a variety of manners as well. For example, the tubular implant 20 may be formed by etching or cutting a pattern from a tube or sheet of stent material; a sheet of stent material may be cut or etched according to a desired stent pattern whereupon the sheet may be rolled or otherwise formed into the desired substantially tubular, bifurcated or other shape. For the tubular implant 20, one or more wires or ribbons of stent material may be woven, braided or otherwise formed into a desired shape and pattern. The tubular implant 20 may include further components that are welded, bonded or otherwise engaged to one another. The tubular implant 20 may include a non-porous, non-permeable biocompatible material, cover or the like, for instance, when the tubular implant 20 is used as a blood flow diverter.

The delivery system 12 includes a delivery catheter 40 having a proximal end portion 42, a distal end portion 44 including an open distal end 46, and a delivery lumen 48 extending between the proximal end portion 42 and the distal end portion 44. The delivery system 12 may also include a pusher member 30 slidably disposed in the delivery lumen 48 of the delivery catheter 40. The pusher member 30 has a proximal end portion 32, a distal end portion 34, and a guidewire lumen 36 extending therebetween. The tubular implant 20 is disposed within the delivery catheter 40 and disposed distal of the pusher member 30, so that the pusher member 30 can prevent proximal movement of the tubular implant 20 as the delivery catheter 40 is moved proximally for deployment of the tubular implant 20 out of the open distal end tip 46 of the delivery catheter 40, i.e., unsheathing the tubular implant 20 while the distal end 24 of the implant 20 remains at approximately the same location in the vessel 90) (FIG. 3B-D), as described in more detail below.

Alternatively or additionally, the distal end portion 34 of the pusher member may comprise an actuator 85, including mechanical detachment interfaces, such as inflatable balloons, releasable interlocking geometries, mechanical fastening, or electrolytically actuated release mechanisms, or the like or combinations thereof, for deployment of the tubular implant 20 out of the distal end tip 46 of the delivery catheter (not shown). When the actuator 85 includes a balloon, the balloon is in fluid communication with guidewire lumen 36 for inflation and deflation. An inflation source and/or vacuum (not shown) is fluidly coupled to the guidewire lumen 36 to deliver and withdraw fluid and/or gas to and from the balloon or the distal end tip 46 of the delivery catheter 40.

The tubular implant delivery system 12 includes side-arm adapters 14 and 16 in fluid communication with the delivery lumen 48 of delivery catheter 40 and the guidewire lumen 36 of the pusher member 30, respectively. The side-arm adapters 14 and 16 are configured to be coupled to syringes, fluid and/or vacuum sources (not shown). The delivery catheter 40 may have a full length of about 50-300 cm, and typically about 60-200 cm. The delivery catheter 40 is configured for accessing a blood vessel or body lumen 90 for a desired treatment in a target site. For example, the target site may be within a small diameter blood vessel having a 2-5 mm lumen diameter and accessible by way of a tortuous vessel path which may involve sharp vessel turns and multiple vessel branches. In such cases, the delivery system 12, particularly the delivery catheter 40, has a suitably small diameter and flexible construction.

Further, the delivery system 12 may also include a guidewire 80 having a proximal portion 82 and a distal portion 84. Generally, the proximal portion 82 may be formed from material that is stiffer than the distal portion 84 of the guidewire 80, so that the proximal portion has sufficient pushability to advance the guidewire 80 through the patient's vascular system, while the distal portion 84 may be formed of a more flexible material that remains flexible and tracks more easily to access remote locations in tortuous regions of the vasculature. In some instances, the proximal portion 82 of the guidewire 80 may include a reinforcement layer, such as a braided layer or coiled layer to enhance the pushability of the guidewire 80. When using the delivery systems 12, the delivery catheter 40, the pusher member 30 and the implant are introduced into the patient over the guidewire 80, which has been previously introduced. The guidewire 80 may extend through the entire length of the delivery catheter 40 and pusher member 30 through the lumen 36 (see FIG. 1). Alternatively, the guidewire 80 may extend through only a distal portion of the delivery catheter 40 and pusher member 30, in the so called "rapid-exchange" delivery systems (not shown).

Referring back to delivery catheter 40, the distal end portion 44 of the delivery catheter 40 comprises a radiopaque first marker 52 on the distal end of the delivery catheter 40 (also referred to as the "catheter distal end marker 52"). (see FIGS. 1-3E). The catheter distal end marker 52 is formed of a one or more radiopaque, biocompatible materials, such as platinum, gold, tungsten, or alloys thereof or other metals. The catheter distal end marker 52 on the delivery catheter 40 also overlies or otherwise indicates a location of the distal end 24 of the tubular implant 20 when the tubular implant 20 is loaded into the delivery catheter 40 in a ready-to-deploy position in the delivery system 12 (FIGS. 1, 3A-B).

As used in this specification, the term "ready-to-deploy position" refers to the location of the implant 20 within the catheter distal end portion 44 in close proximity to the open distal end tip 46 (as shown in FIG. 1), just prior to deployment of the implant into the body lumen 90 by withdrawing the delivery catheter 40 relative to the implant 20, while the implant 20 is prevented from moving proximally by the pusher member 30. Thus, the distal end 24 of the implant 20, when in a "ready-to-deploy position" in the delivery catheter 40, is at a same or substantially same location as the distal end 24 of the implant 20 will be when deployed out of the delivery catheter 40. Additionally, the distal end 24 of the implant 20 may include a radiopaque marker (not shown) configured to assist with the overlying and location matching of the distal end 24 of the implant 24 with the distal marker 52\of the delivery catheter 40. The implant can be placed in the "ready-to-deploy position" in the delivery catheter 40 before the delivery catheter 40, the pusher member 30 and the implant 20 are introduced into the patient over the guidewire 80 as a unit, as described in detail below. Alternatively, the delivery catheter 40 can be introduced into the patient before the implant 20 and the pusher member 30 are introduced into the proximal end portion 42 of the delivery catheter 40 and pushed to the distal end portion 44. In these latter embodiments, a radiopaque marker on the distal end 24 of the implant 20 facilitates in vivo alignment of the distal end 24 of the implant 20 with the distal end 46 (and catheter distal end marker 52) of the catheter 40.

Figure 3A:
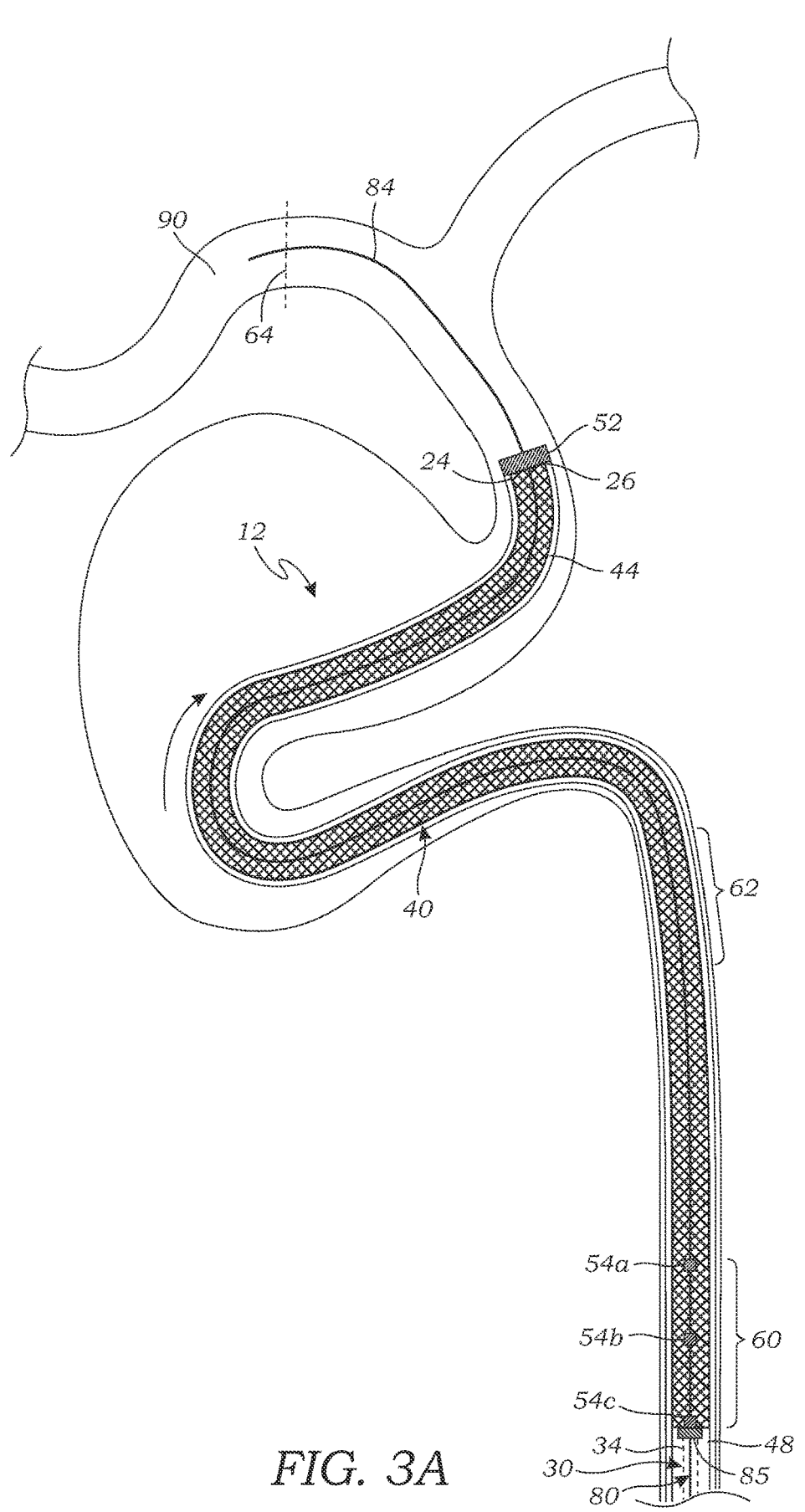
FIGS. 3A-3E are cross-sectional views of a method of delivering a tubular implant into a target site of a patient using the implant delivery system of FIG. 1.
Figure 3B:
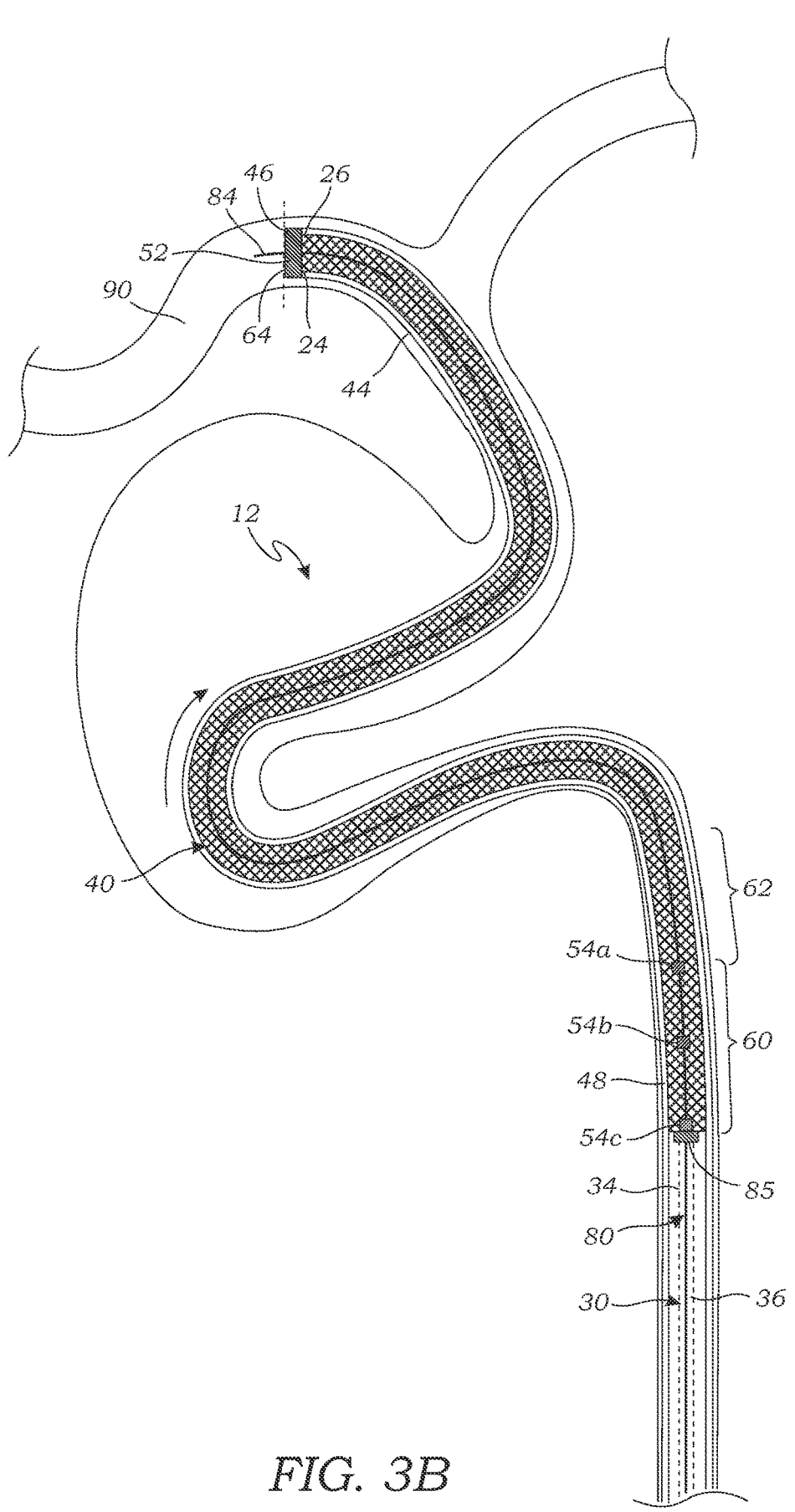
Figure 3C:
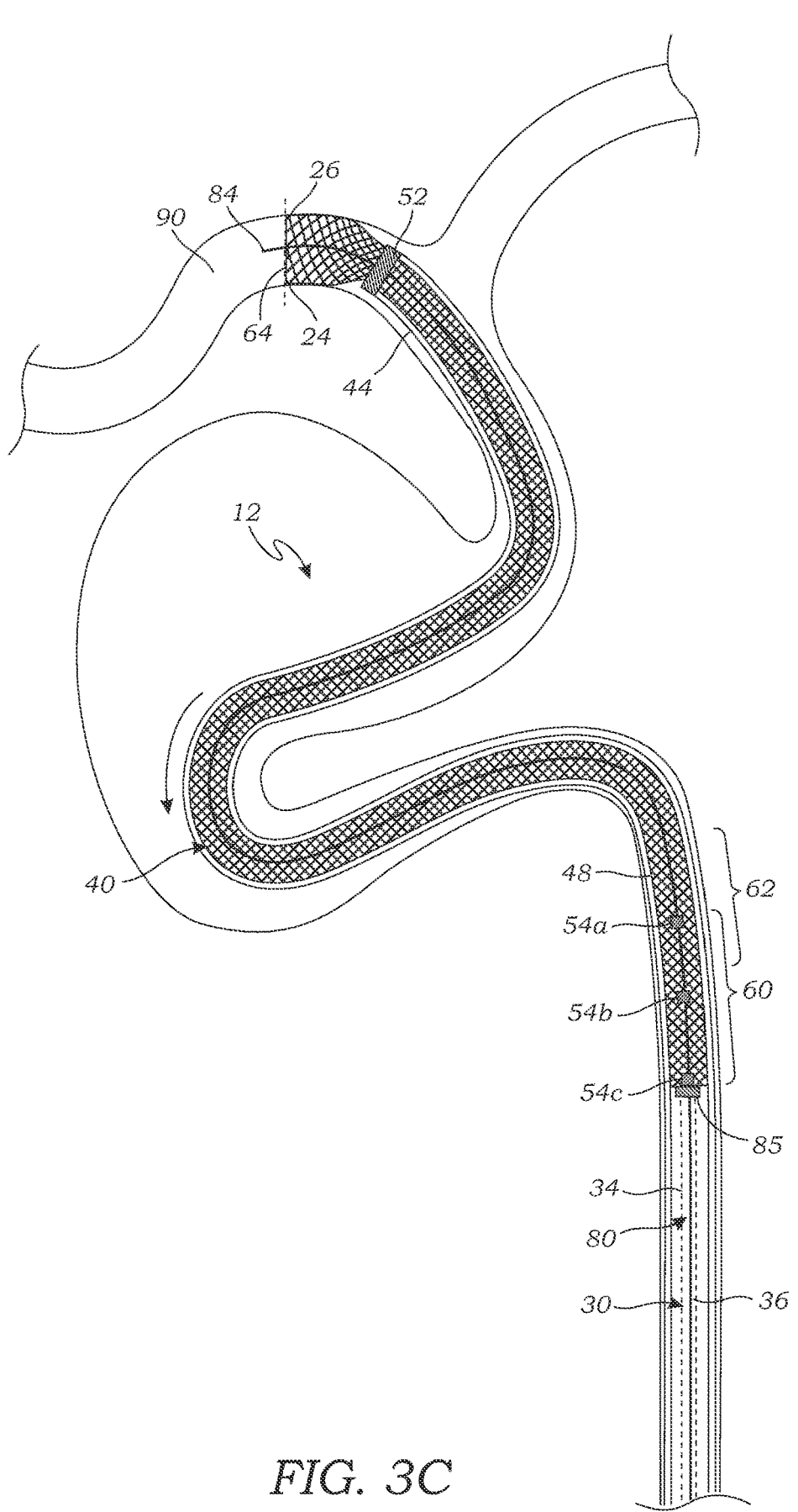

The catheter distal end marker 52 can be used to identify the distal landing location of the distal end 24 of the tubular implant 20 if the implant is implanted in a body lumen 90 at any point in time, by withdrawing the delivery catheter 40 relative to the implant 20 (FIGS. 1, 3B-3C). Thus, a clinician may select a desired (or "target") distal landing location by observing the body lumen 90 on an imaging device (e.g., a fluoroscope), and maneuvering the delivery catheter 40 until the distal marker 52 is positioned at the target distal landing location.

The implant delivery system 12 also has one or more implant markers 54, including, a second marker 54a, a third marker 54b, and a fourth marker 54c (referred to collectively as "implant markers 54") disposed on the implant delivery system 12. (FIGS. 1-3). The implant markers 54 may be disposed on the tubular implant 20, or on the delivery wire 80, or other suitable structure of the implant delivery system 12. The implant markers 54 are configured such that the catheter distal end marker 52 moves relative to the implant markers 54 as the delivery catheter 40 is moved proximally relative to the tubular implant 20 to deploy the tubular implant 20 out of the open distal end tip 46 of the delivery catheter 40 and into a body lumen 90. The following description will describe the implant markers 54 as being disposed on the tubular implant 20, with the understanding that the implant markers 54 may be disposed on any suitable structure of the implant delivery system 12. The implant markers 54 are also formed of one or more radiopaque, biocompatible materials, such as platinum, gold, tungsten, or alloys thereof or other metals.

The second marker 54a (also referred to as the "last proximal portion marker 54a") is positioned on the tubular implant 20 to indicate the distal end of a last proximal portion 60 of the tubular implant 20. The last proximal portion 60 of the tubular implant is a smaller length of the tubular implant 20 which can be used by a physician to determine a proximal landing location 62 of the proximal portion 22 of the tubular implant 20 when the delivery catheter 40 has been withdrawn from the tubular implant up to the position of the last proximal portion marker 54a. For instance, a delivery length of last proximal portion 60 in the collapsed, delivery configuration LPP1 is typically 5-10 mm long (or 5-20 mm long), and the implanted, foreshortened length of the last proximal portion 60 in the radially expanded, implanted configuration LPP2 is typically about 2-5 mm long (or 2-10 mm long). (see FIGS. 1, 2A, 2B, 3A, 3B). As explained herein, the amount of foreshortening of the last proximal portion 60 depends on the cross-section of the body lumen 90 at the proximal landing location 62 of the last proximal portion 60 of the body lumen 90. As an example, in the case that the diameter of the tubular implant 20 in the collapsed, delivery configuration is 2 mm, and the cross-section of the body lumen 90 at the proximal landing location 62 is 5 mm, the tubular implant 20 may foreshorten by 50%. As described herein, the amount of foreshortening of the last proximal portion 60, and thus the foreshortened, deployed length of the last proximal portion 60 may be determined by determining the cross-section of the proximal landing location 62 of the body lumen 90. In such case, for a last proximal portion 60 having a delivery configuration length LPP1 of 10 mm, the foreshortened, deployed length LPP2 in the body lumen 90 will be 5 mm.

In an alternative embodiment, the last proximal portion marker 54a may be an axially elongated marker 54a having a distal end at the distal end of the last proximal portion, and extending axially to a proximal end which is proximal of the distal end. For example, the last proximal portion marker can be a solid line marker disposed on the tubular implant 20, or it could be a coating of marker material on the delivery wire 80. The axially elongated marker 54a may have a known length, such as 5 mm or 10 mm, such that it provides a visual gauge to the physician.

Methods for determining the foreshortened, deployed length LPP2 of the last proximal portion 60 in a proximal landing location 62 will now be described. In a first method, an actual cross-section of the body lumen 90 at a predicted proximal landing location 62 in the body lumen 90 is determined. For instance, the cross-section may be measured using any suitable means, such as visualization with an imaging system, including an external imaging system or an imaging catheter system inserted into the body lumen 90 at the predicted proximal landing location 62, or a gauge, etc. The determined cross-section is then used to determine the foreshortened, delivery length LLP2 of the last proximal portion 60 of the tubular implant 20. The foreshortened, delivery length LLP2 may be determined using the dimensions and physical characteristics of the tubular implant 20, a foreshortening chart generated by empirical data on the foreshortening of the tubular implant 20 as a function of the cross-section into which it is deployed, etc. In another method, the cross-section of the body lumen 90 at a predicted proximal landing location 62 in the body lumen 90 may be an estimate based on "typical" dimensions (e.g., a "standard" cross-sectional diameter) of the particular body lumen. For example, a "standard" cross-section of a section of a cerebral artery that is a frequent location for a stenting procedure is about 4 mm. Thus, taking into consideration this standard cerebral artery cross-section of 4 mm and the dimensions and characteristics of the tubular implant 20, a deployed length LPP2 of the last proximal portion 60 in a proximal landing location 62 can be determined same or similar as using an actual, measured cross-section.

In an alternative embodiment, the last proximal portion marker 54a may be adjustably locatable on the tubular implant 20. In this embodiment, the axial position of the last proximal portion marker 54a can be set to a determined deployed length of the last proximal portion 60. For example, it may be desired for a physician to be able to visualize when there is a determined deployed length LPP2 of a last proximal portion 60 in a proximal landing location 62 of 5 mm. The cross-section of the proximal landing location 62 of the body lumen 90 is first determined, and then the length of the last proximal portion 60 in the collapsed, delivery configuration LPP1 which will foreshorten to the determined deployed length LPP2 of 5 mm is determined based on the cross-section of the proximal landing location 62 (and the diameter and physical characteristics of the tubular member 20). The last proximal portion marker 54a is then located at the determined length LPP1 distally from the proximal end 22 of the tubular member.

The third marker 54b (also referred to as the "re-sheath marker 54b") is positioned on the tubular implant 20 to indicate a position of the proximally withdrawn delivery catheter 40 at which the delivery catheter cannot be advanced in the opposite direction to re-sheath the tubular implant 20. For example, if the physician determines that the landing location of the tubular implant 20 within the body lumen is in a clinically undesirable location, or there is some other complication during the implantation procedure, the physician can re-sheath the tubular implant 20 into the delivery catheter by advancing the delivery catheter 40 distally back over the deployed portion of the tubular member 20, such that the tubular implant returns to the collapsed, delivery configuration within the delivery catheter 40. The physician may then re-position the implant delivery system 12 within the body lumen 90, or remove the implant delivery system 12 from patient. As shown in the illustrated embodiment, the re-sheath marker 54*b* is positioned proximally from the last proximal portion marker 54*a*. This allows the delivery catheter 40 to be proximally withdrawn at least to the last proximal portion marker 54*a*, where the physician can determine the proximal landing location 62 of the last proximal portion 60, and re-sheath and reposition the implant delivery system 12 if it is clinically undesirable. Alternatively, the re-sheath marker 54*b* can be positioned distally of the last proximal portion marker 54*a*, in which case, if the delivery catheter is withdrawn to the last proximal portion marker 54*a*, the tubular member 20 cannot be re-sheathed because the delivery catheter 40 will have been withdrawn past the re-sheath marker 54*b*.

The fourth marker 54*c* (also referred to as the "implant proximal end marker 54*c*") is positioned on the proximal end of tubular member 20. The implant proximal end marker 54*c* allows the physician to visualize the location of the proximal end of the tubular member 20 during an implantation procedure.

FIG. 1 illustrates the implant delivery system 12 in the ready-to-deploy configuration with the tubular implant 20 in the collapsed, delivery configuration and fully inserted into the delivery lumen 48 of the delivery catheter 30. The distal end 24 of the tubular implant 20 is axially aligned with the catheter distal end marker 52 (if the tubular implant 20 has an implant distal end marker, then it is axially aligned with the catheter distal end marker 52).

Figures 2A, 2B:
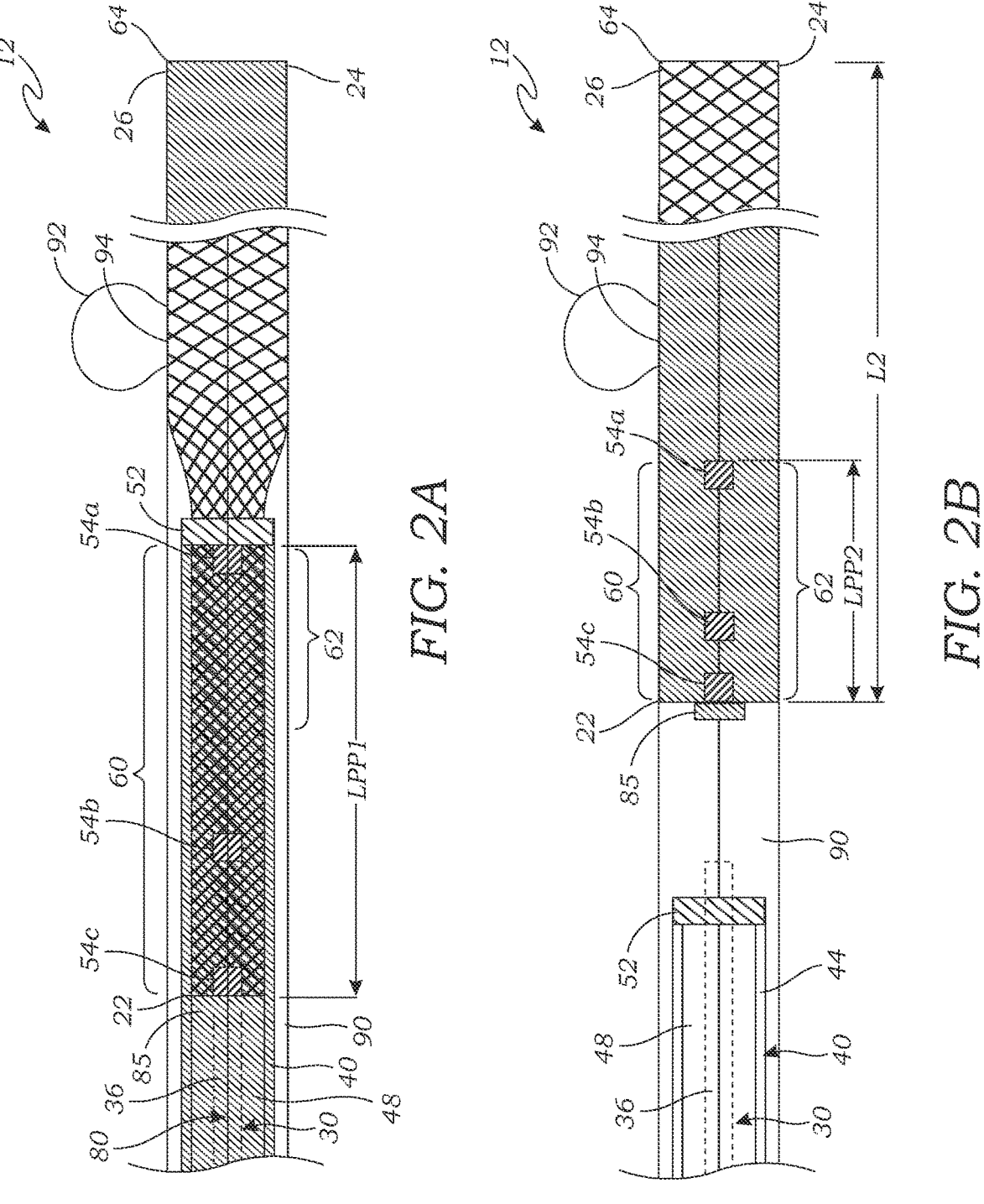
FIGS. 2A and 2B are partial cross-sectional views of the implant delivery system of FIG. 1 depicting a method of deploying the tubular implant from the delivery catheter into a target site of body lumen using the implant delivery system of FIG. 1.

Referring to FIGS. 2A and 2B, a method of using the medical system 10 and implant delivery system 12 to implant a tubular implant 20 into a body lumen 90 will now be described. FIG. 2A illustrates the implant delivery system 12 of FIG. 1 with the delivery catheter 40 partially withdrawn axially thereby deploying the distal portion 24 of the tubular member 20. Accordingly, the distal portion 24 of the tubular member 20 is in the radially expanded, implanted configuration. After gaining access to the vasculature region of a patient, the delivery catheter 40, with the tubular implant inserted therein, and the pusher member 30 are introduced into the patient over the guidewire 80, which has been previously introduced into the body lumen 90. The delivery catheter 40 is advanced until the catheter distal end marker 52 is located adjacent a target distal landing location 64 for the tubular implant 20, for example, beyond the neck 94 of an aneurysm 92. The clinician then withdraws the delivery catheter 40, while the pusher member 30 holds the tubular member 20 in position such that tubular member 20 is deployed out of the open distal end 46 of the delivery catheter 40. As shown in FIGS. 1 and 2B, the actual, full implanted length L2 of the tubular implant 20 in its expanded, implanted configuration is shorter than the full delivery length L1 in the radially constrained and collapsed configuration. In FIG. 2A, the delivery catheter 40 is withdrawn to the point that the catheter distal end marker 52 reaches the last proximal portion marker 54*a*, such that only the last proximal portion 60 of the tubular member 20 remains to be deployed from the delivery catheter 40. At this position of the delivery catheter 40, it is known that the last proximal portion 60 will extend the determined, foreshortened deployed length LPP2 in the proximal direction from the last proximal portion marker 54*a* (and also from the catheter distal end marker 52). Accordingly, the clinician can visualize the actual proximal landing location 62 of the last proximal portion 60 of the tubular implant 20. The clinician can determine if the actual proximal landing location 62 of tubular implant 20 is clinically desirable. As can be seen in FIG. 2A, the delivery catheter 40 has not yet been withdrawn past the point that the tubular implant 20 can be re-sheathed, as indicated by the catheter distal end marker 52 remaining distal of the re-sheath marker 54*b*. If the clinician determines that the actual proximal landing location 62 of the tubular implant 20 is not clinically desirable, the clinician can re-sheath the tubular implant 20 by advancing the delivery catheter 40 distally, while using the pusher member 30 to hold the tubular implant 20 in position relative to the delivery catheter 40. Once the tubular implant 20 is fully re-sheathed (i.e., the delivery catheter 40 is advanced until the catheter distal end marker 52 is adjacent the distal end of the 24 of the tubular implant 20, and the tubular implant 20 is again in the radially constrained and collapsed configuration, the clinician can re-position the implant delivery system 12. If the actual proximal landing location 62 of the tubular implant 20 is determined to be clinically desirable, then the clinician can continue to withdraw the delivery catheter 40 to deploy the last proximal portion 60 of the tubular implant 20.

FIG. 2B illustrates the implant delivery system 12 with the delivery catheter 40 fully withdrawn axially thereby deploying the entire tubular member 20, such that the last proximal portion 60 is also deployed in the body lumen 90 and is in the radially expanded, implanted configuration, and the last proximal portion 60 has now foreshortened to the determined, deployed length LPP2. The tubular implant 20 is also detached from the pusher member 30, such as by using the actuator 85 to detach the tubular member 20.

Turning to FIGS. 3A-3E, a method of using the medical system 10 and implant delivery system 12 to delivery and implant to a target site in a body lumen 90 using the delivery system 12. The foreshortened length LPP2 of the last proximal portion 60 of the tubular member 20 is determined, or set, as described herein. This will allow the clinician to accurately determine the proximal landing location 62 of the last proximal portion of the implanted tubular member 20, as described below.

The guidewire 80 is first advanced through the vasculature region of a patient and is positioned along the desired landing location for the tubular implant 20 within the body lumen 90, such that the distal end 84 of the guidewire 80 is distal of the target distal landing location 64 of the body lumen. As shown in FIG. 3A, the delivery catheter 40 having the tubular implant 20 loaded within the delivery lumen 48 in its radially constrained and collapsed configuration, is inserted into the body lumen 90. The tubular implant 20 is fully inserted into the delivery catheter 40 such that the distal end 24 of the tubular member 20 is adjacent the catheter distal end marker 52. The delivery catheter 50 and tubular implant 20 are advanced into the body lumen 90 over the guidewire 80 with the guidewire 80 positioned in the guidewire lumen 36 of the pusher member 30.

As shown in FIG. 3B, the implant delivery system 12 is advanced until the catheter distal end marker 52 indicates that the location of the distal end 24 of the tubular implant 20 is positioned adjacent a target distal landing location 64 for the distal end 24 of the tubular implant 20 when implanted in the body lumen 90. The clinician may visualize the position of the catheter distal end marker 52 using a suitable imaging system.

As illustrated in FIG. 3C, the delivery catheter 40 is withdrawn proximally relative to the pusher member 30 thereby delivering the tubular implant 20 out through open distal end 46 of the delivery catheter 40 and into the body lumen 90, so that the distal end 24 of the implant 20 stays in substantially the same location as the target distal landing location 64. As the tubular implant 20 is delivered out of the delivery catheter 40, the tubular implant 20 expands radially outward, and foreshortens.

Figure 3D:
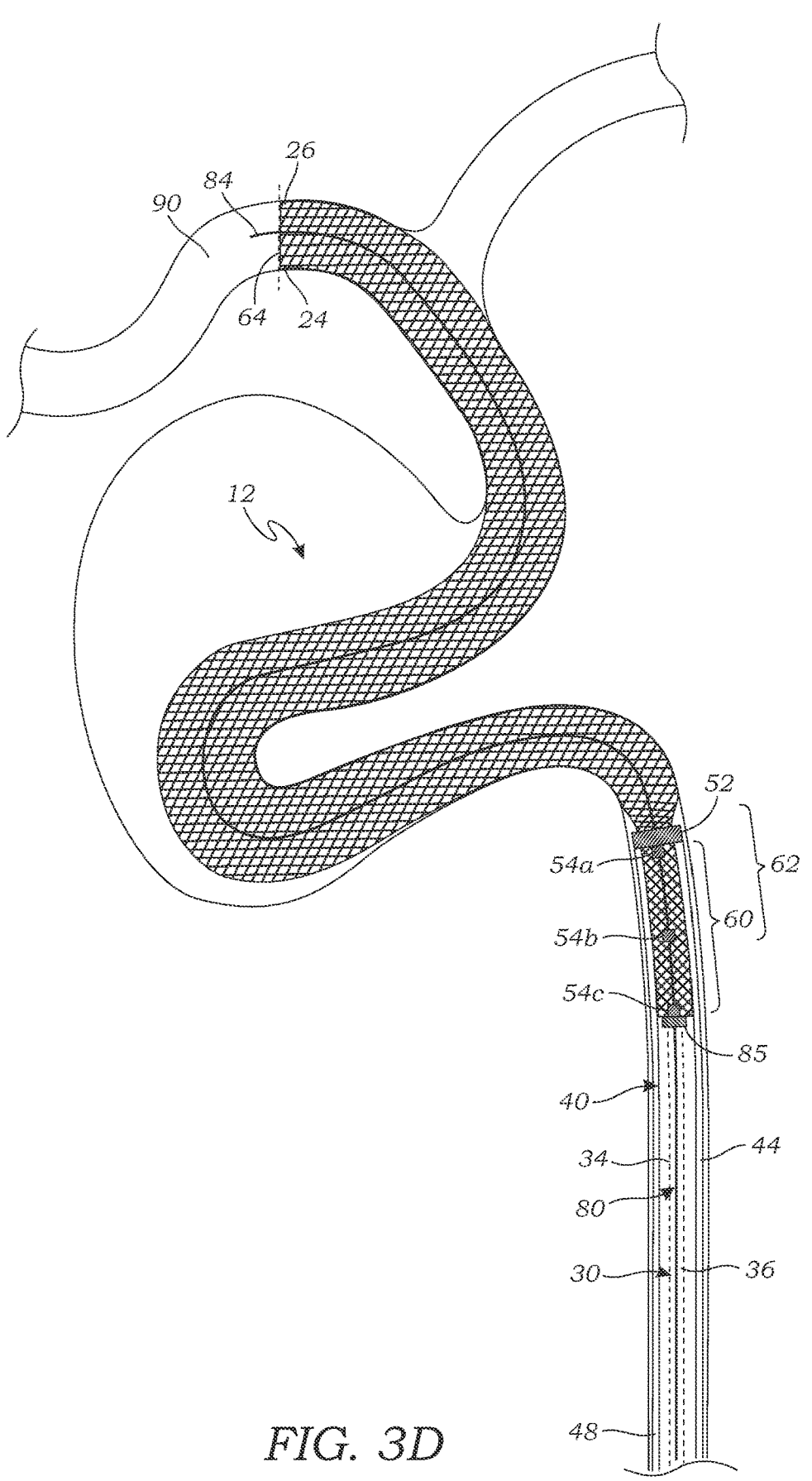

As shown in FIG. 3D, the delivery catheter 40 is continued to be withdrawn relative to the pusher member 30 to the point that the catheter distal end marker 52 reaches the last proximal portion marker 54a, such that only the last proximal portion 60 of the tubular member 20 remains to be deployed from the delivery catheter 40. At this position of the delivery catheter 40, it is known that the last proximal portion 60 upon deployment out of the delivery catheter 40 will extend the determined, foreshortened deployed length LPP2 in the proximal direction from the last proximal portion marker 54a (and also from the catheter distal end marker 52). Accordingly, the clinician can visualize the actual proximal landing location 62 of the last proximal portion 60 of the tubular implant 20. The clinician can determine if the actual proximal landing location 62 of tubular implant 20 is clinically desirable.

As also depicted in FIG. 3D, the delivery catheter 40 has not yet been withdrawn past the point that the tubular implant 20 can be re-sheathed, which is indicated by the catheter distal end marker 52 still being distal of the re-sheath marker 54b.

With the delivery catheter 40 in the position of FIG. 3D, the clinician determines whether the actual proximal landing location 62 of the tubular implant 20 within the body lumen 90 is clinically desirable. Since the foreshortened deployed length LPP2 of the last proximal portion 60 is known, the clinician can visualize the actual proximal landing location 62 of the tubular implant 20 within the body lumen 90.

If the clinician determines that the actual proximal landing location 62 of the tubular implant 20 within the body lumen 90, then the clinician may re-sheath the tubular implant 20 by advancing the delivery catheter 40 distally, while using the pusher member 30 to hold the tubular implant 20 in position relative to the delivery catheter 40. Once the tubular implant 20 is fully re-sheathed (i.e., the delivery catheter is advanced until the catheter distal end marker 52 is adjacent the distal end of the 24 of the tubular implant 20), and the tubular implant 20 is again in the radially constrained and collapsed configuration, the clinician re-positions the implant delivery system 12, or may even remove the implant delivery system 12 and re-start the procedure.

Figure 3E:
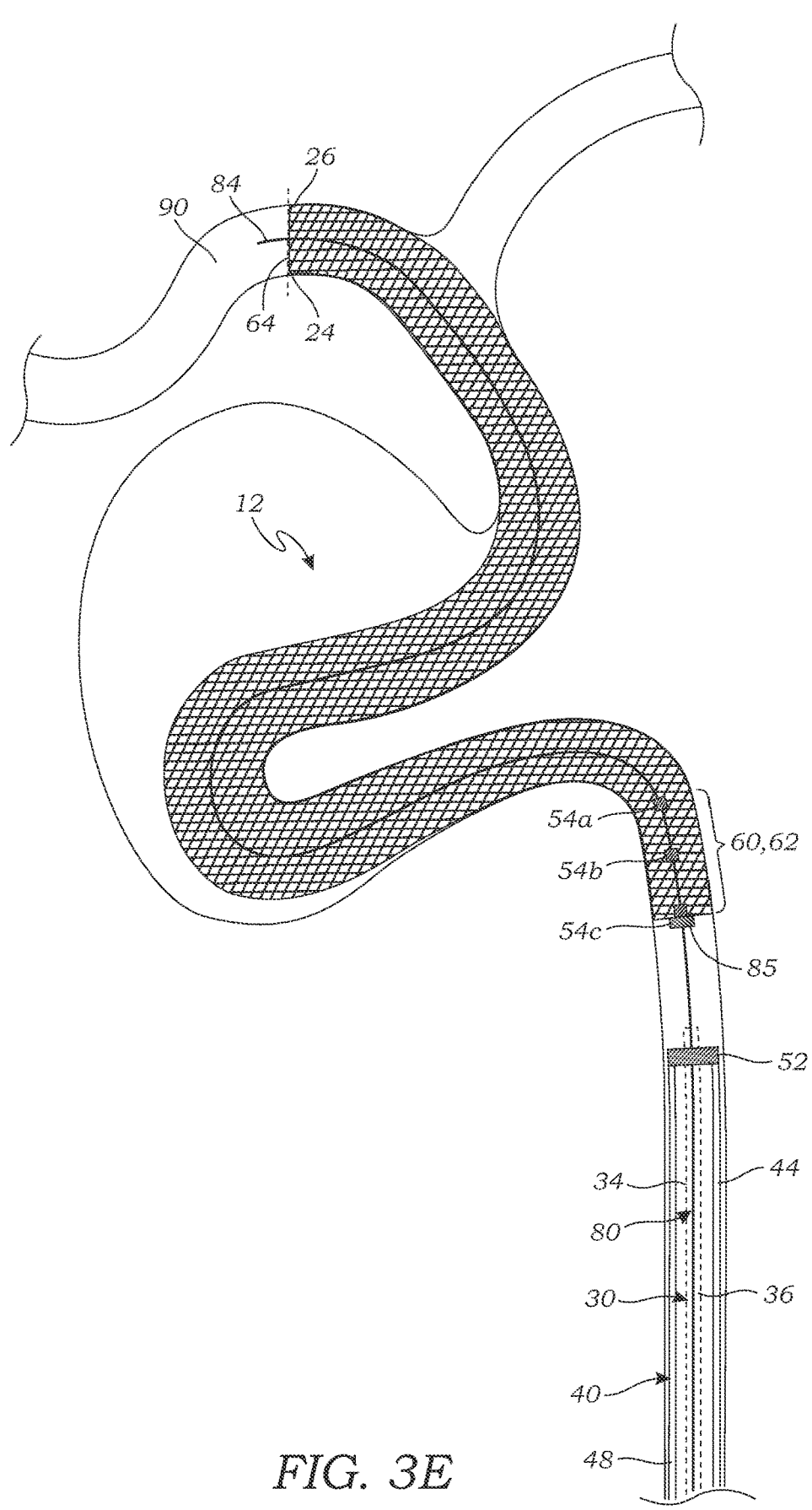

As shown in FIG. 3E, if the actual proximal landing location 62 of the tubular implant 20 is determined to be clinically desirable, then the clinician continues to withdraw the delivery catheter 40 relative to the pusher member 30 to deploy the last proximal portion 60 of the tubular implant 20. The delivery catheter 40 fully withdrawn from the tubular implant 20, such that the last proximal portion 60 is also deployed in the body lumen 90. The last proximal portion 60 expands to the radially expanded, implanted configuration, such that the last proximal portion 60 has foreshortened to the determined, deployed length LPP2. The tubular implant 20 is then detached from the pusher member 30, such as by using the actuator 85 to detach the tubular member 20, as also shown in FIG. 3E. The tubular member 20 is now fully implanted within the body lumen 90. The remainder of the implant delivery system 12 can now be fully withdrawn from the body lumen 90, leaving the tubular member implanted within the body lumen 90.

In still another embodiment, a selection of implant delivery systems 12 comprising a plurality of delivery systems 12 is provided in which each of the delivery systems 12 is configured for a different cross-section (i.e., cross-section diameter) of the proximal landing location 62 of the body lumen 90. The axial position of the proximal portion marker 54a is set on each respective delivery system 12 to provide a predetermined deployed length LPP2 of the last proximal portion 60 for a given cross-section of proximal landing location 62 of the body lumen 90. For instance, a set of implant delivery systems 12 may be configured to provide a predetermined deployed length LPP2 of 5 mm for various different cross-sections, such as for cross-section diameters of 3.0 mm, 3.5 mm, 4.0 mm, 4.5 mm, 5.0 mm, etc. In other words the set would include a first implant delivery system 12 for a 3.0 mm cross-section diameter having the proximal portion marker 54a axially positioned such that the deployed length LPP2 in a 3.0 mm lumen is 5 mm, a second implant delivery system 12 for a 3.5 mm cross-section diameter having the proximal portion marker 54a axially positioned such that the deployed length LPP2 in a 3.5 mm lumen is 5 mm, a third implant delivery system 12 for a 4.0 mm cross-section diameter having the proximal portion marker 54a axially positioned such that the deployed length LPP2 in a 4.0 mm lumen is 5 mm, and so on.

A method of selecting and using an implant delivery system 12 from the set of a plurality of implant delivery system 12 is as follows. First, the cross-section of the proximal landing location 62 of the body lumen 90 is determined. Then, the clinician selects one of the implant delivery systems 12 from the set which best corresponds to the determined cross-section. For instance, if the determined cross-section is 4.0 mm, then the 4.0 mm implant delivery system 12 is selected. Then, the selected implant delivery system 12 is used according to the same method described above with respect to FIGS. 3A-3E.

Figure 4:
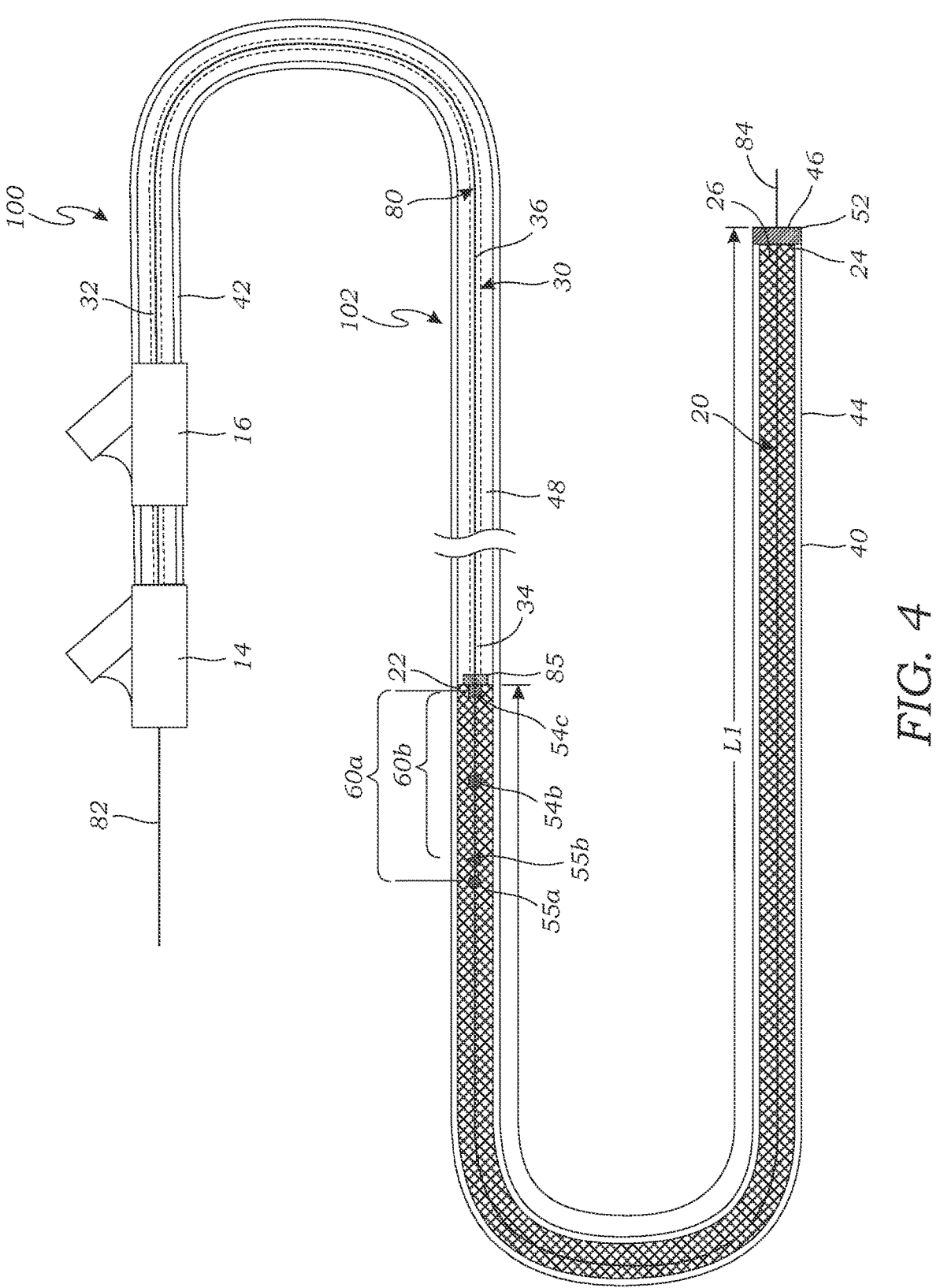
FIG. 4 is a side view of a medical assembly including a ranged implant delivery system for delivering a tubular implant, according to another embodiment of the disclosed inventions.
Figures 5A, 5B:
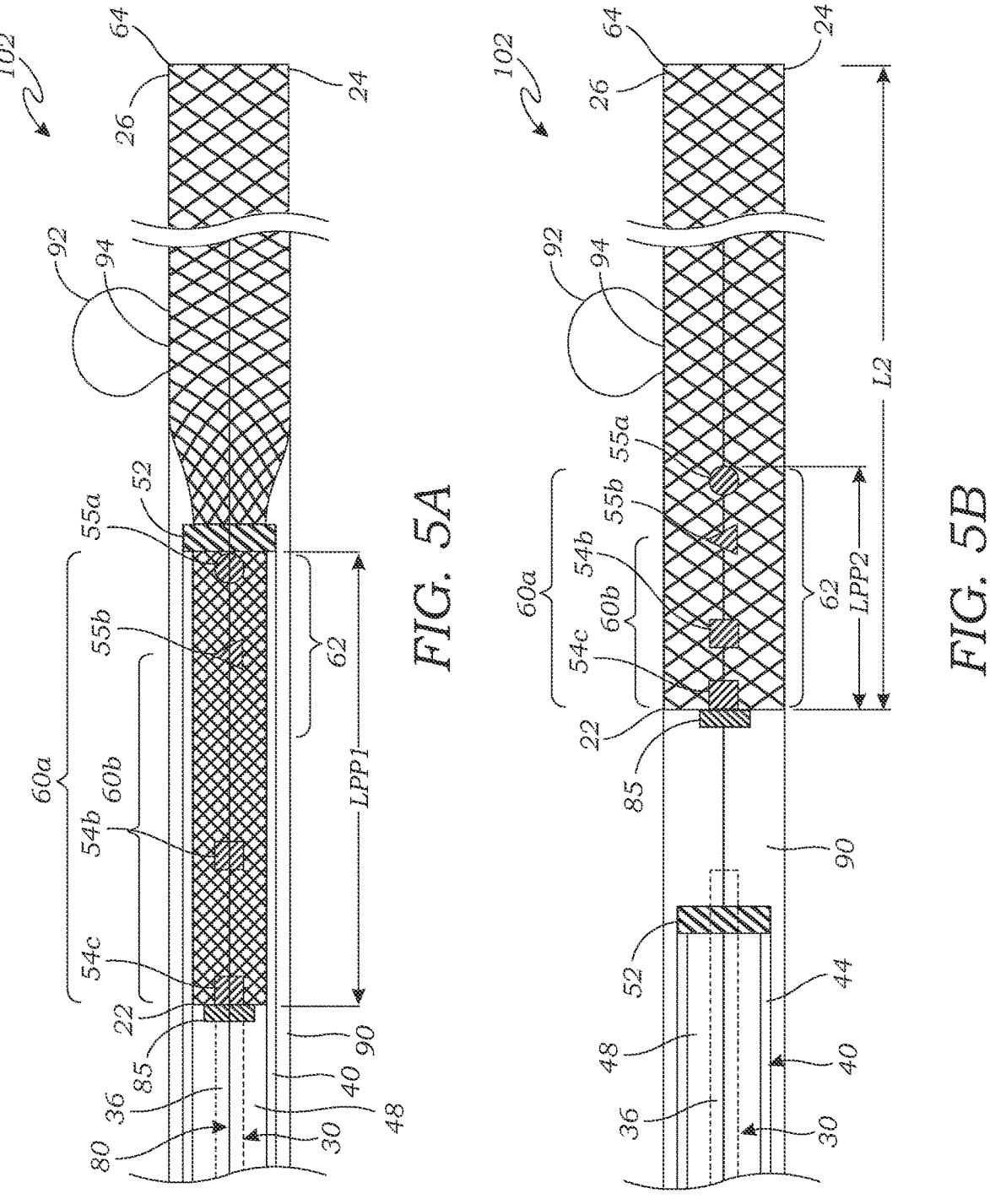
FIGS. 5A and 5B are partial cross-sectional views of the ranged implant delivery system of FIG. 4 depicting a method of deploying the tubular implant from the delivery catheter into a target site of body lumen using the implant delivery system of FIG. 1.

Turning to FIGS. 4 and 5A-5B, another medical assembly 100 for delivering an expandable tubular implant 20 into a target site of a patient is shown, according to another embodiment of the disclosed inventions. The medical assembly 100 is very similar to the medical assembly 10 described above, except that it includes a delivery system 102 (also referred to as a "ranged implant delivery system 102") which has a tubular implant 20 having two proximal portion markers 55a and 55b instead of a single proximal portion marker 54a. The two proximal portion markers 55a and 55b are axially positioned to provide a predetermined deployed length LPP2 for a range of cross-sections of the proximal landing location 62 of the body lumen 90. The first proximal portion marker 55a and second proximal portion marker 55b may have different shapes or different radiopaque indications to visually distinguish the markers from each other. The first proximal portion marker 55a and second proximal portion marker 55b are positioned at different axial locations on the tubular implant 20. In this example, the first proximal portion marker 55a is positioned axially distal of the second proximal portion marker 55b. The first proximal portion marker 55a defines a last proximal portion 60a, and the second proximal portion marker 55b defines a last proximal portion 60b. As the first proximal portion marker 55a is distal of the second proximal portion marker 55b, the first proximal portion marker will indicate a given deployed length for a larger diameter cross-section than the second proximal portion marker 55b. This is because the last proximal portion for a larger diameter cross-section of the proximal landing location 62 will foreshorten proportionally more than for a smaller diameter cross-section. For instance, the first proximal portion marker 55*a* may provide a predetermined deployed length (e.g., 5.0 mm) in a first cross-section of the proximal landing location 62 (e.g., 4.0 mm), and the second proximal portion marker 55*b* may provide the predetermined deployed length (e.g., 5.0 mm) in a second cross-section less than the first cross-section (e.g., 3.5 mm). Accordingly, in this example, the medical assembly 100 having this tubular implant 20 is configured to provide a nominal predetermined deployed length of about 5.0 mm for the range of cross-sections from 3.5 mm to 4.0 mm.

In still another embodiment, a selection of ranged implant delivery systems 102 may be provided similar to the selection of implant delivery systems 12, described above. Each of the delivery systems 102 in the set of a plurality of delivery systems is configured for a different range of cross-sections (i.e., range of cross-section diameters) of the proximal landing location 62 of the body lumen 90. Accordingly, the axial positions of the two proximal portion markers 55*a* and 55*b* are set on each respective delivery system 102 to provide a predetermined deployed length LPP2 for a given range of cross-sections of proximal landing location 62 of the body lumen 90. For instance, a set of implant delivery systems 12 may be configured to provide a predetermined deployed length LPP2 of 5 mm for various different ranges of cross-sections, such as for cross-section diameters of 3.0-3.5 mm, 3.5-4.0 mm, 4.0-4.5 mm, 4.5-5.0 mm, 5.0-5.5 mm, etc. In other words the set would include a first implant delivery system 12 for a 3.0-3.5 mm range of cross-section diameter having the proximal portion markers 55*a* and 55*b* axially positioned such that the deployed length LPP2 in a 3.0-3.5 mm lumen is 5 mm, a second implant delivery system 102 for a 3.5-4.0 mm range cross-section diameter having the proximal portion markers 55*a* and 55*b* axially positioned such that the deployed length LPP2 in a 3.5-4.0 mm lumen is 5 mm, a third implant delivery system 102 for a 4.0-4.5 mm cross-section diameter having the two proximal portion markers 55*a* and 55*b* axially positioned such that the deployed length LPP2 in a 4.0-4.5 mm lumen is 5 mm, and so on.

A method of selecting and using a ranged implant delivery system 102 from the set of a plurality of implant delivery systems 102 is as follows. First, the cross-section of the proximal landing location 62 of the body lumen 90 is determined. Then, the clinician selects one of the implant delivery systems 102 from the set having a range which includes or encompasses the determined cross-section. For instance, if the determined cross-section is 4.2 mm, then the 4.0-4.5 mm implant delivery system 102 is selected. Then, the selected implant delivery system 102 is used substantially according to the same method described above with respect to FIGS. 3A-3E, except that the proximal portion markers 55*a* and 55*b* will indicate when the delivery catheter has been withdrawn to the point of the last proximal portion 60. The position of the catheter distal end marker 52 at which the determined, foreshortened length LPP2 is remaining is based on the determined cross-section. If the determined cross-section is at the top of the range of cross-sections for the selected implant delivery system 102, then the first proximal portion marker 55*a* will indicate that the determined foreshortened length LPP2 remains to be deployed. If the determined cross-section is at the bottom of the range of cross-sections for the selected implant delivery system 102, then the second proximal portion marker 55*b* will indicate that the determined foreshortened length LPP2 remains to be deployed. If the determined cross-section is somewhere within the range of cross-sections for the selected implant delivery system 102, then a position proportionally located between the first proximal portion marker 55*a* and the second proximal portion 55*b* will indicate the determined foreshortened length LPP2 remains to be deployed the Hence, the clinician can estimate the proper position of the catheter distal end marker 52 relative to the first and second proximal portion markers 55*a* and 55*b* and then visualize the actual proximal landing location 62 of the last proximal portion 60 of the tubular implant 20. The clinician can determine if the actual proximal landing location 62 of tubular implant 20 is clinically desirable, and then deploy the tubular member 20, or make positional adjustments if needed, as described above with respect to FIGS. 3A-3E.

Figure 6:
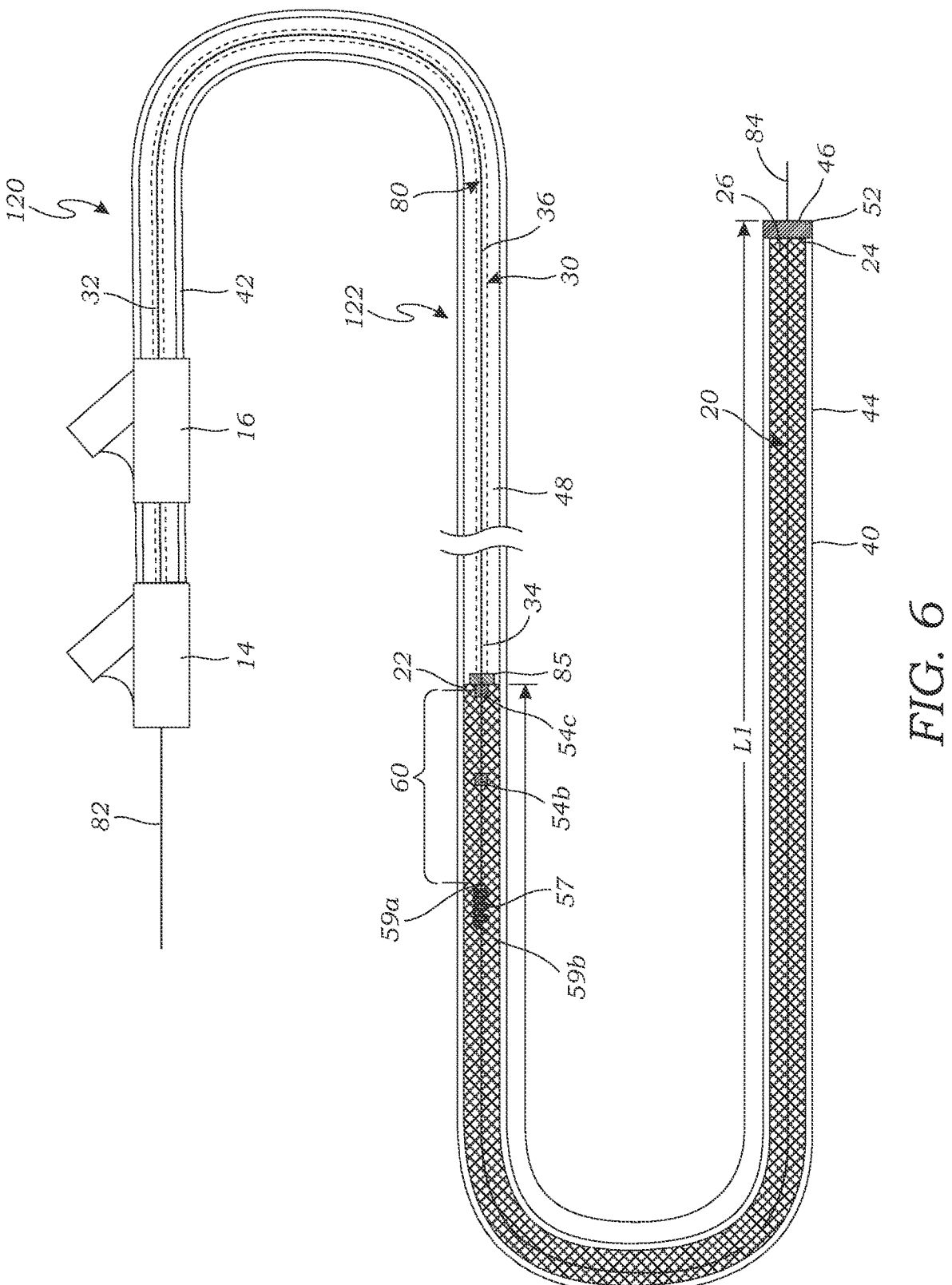
FIG. 6 is a side view of a medical assembly including an implant delivery system for delivering a tubular implant, according to yet another embodiment of the disclosed inventions.
Figures 7A, 7B:
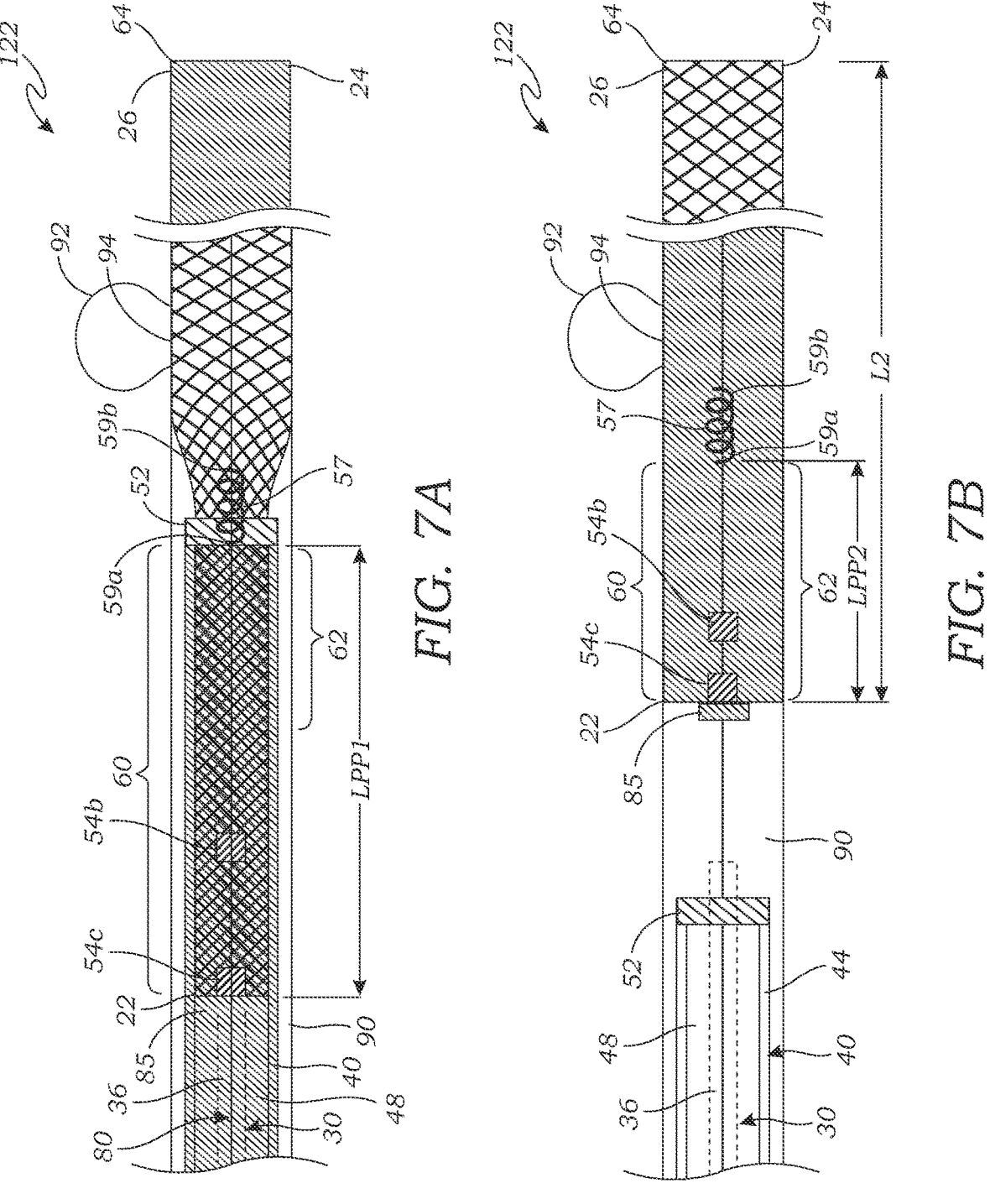
FIGS. 7A and 7B are partial cross-sectional views of the implant delivery system of FIG. 6 depicting a method of deploying the tubular implant from the delivery catheter into a target site of body lumen using the implant delivery system of FIG. 6.

Referring to FIGS. 6 and 7A-7B, another medical assembly 120 for delivering an expandable tubular implant 20 into a target site of a patient is shown, according to another embodiment of the disclosed inventions. The medical assembly 120 is very similar to the medical assembly 10 described above, except that it includes a delivery system 122 which has a tubular implant 20 having a proximal portion marker 57 comprising a radiopaque coil 57. The proximal portion marker 57 is attached to the delivery wire 80 or disposed on the tubular member 20. In the illustrated embodiment in FIGS. 6 and 7A-7B, the coil 57 is positioned such that the proximal end 59*a* of the coil 57 functions as the marker for the proximal portion which indicates that there is a predetermined deployed length LPP2 of the tubular member 20 remaining to be deployed. Alternatively, the proximal portion marker 57 may be axially positioned such that the distal end 59*b* coil 57 functions as the marker for the proximal portion which indicates that there is a predetermined deployed length LPP2 remaining to be deployed.

In another embodiment, the length of the coil 57 may also be configured such that the coil 57 functions similarly to the two markers 55*a* and 55*b* of the ranged implant delivery system 102, in which the proximal end 59*a* of the coil 57 functions like the second proximal portion marker 55*b*, and the distal end 59*b* functions like the first proximal portion marker 55*a*. In this way, the delivery system 122 can be used to the same methods described herein for the delivery system 102.

The methods of using the medical assembly 120 having the delivery system 122 are the same as described herein for the medical assembly 10 having the delivery system 12. Moreover, a set of a plurality of implant delivery systems 122 may be provided similar to the selection of implant delivery systems 12 and 102, described above. A method of selecting and using an implant delivery system 122 from the set of a plurality of implant delivery systems 122 is the same or substantially similar to the methods of selecting and using a set of the implant delivery systems 12 or 102, as described herein.

Although particular embodiments have been shown and described herein, it will be understood that they are not intended to limit the disclosed inventions, and it will be apparent that various changes and modifications may be made (e.g., to the dimensions of various parts) without departing from the scope of the disclosed inventions, which are to be defined only by the claims and their equivalents. For instance, it will be appreciated that elements or components shown with any embodiment herein may be used on or in combination with other embodiments disclosed herein. The specification and drawings are, accordingly, to be regarded in an illustrative rather than restrictive sense.

The invention claimed is:

1. An implant delivery system for implanting a tubular implant in a body lumen, comprising:

a delivery catheter comprising an elongated tubular member having a lumen, a proximal end and open distal end;

a first radiopaque marker disposed on the distal end of the delivery catheter;

a tubular implant disposed within the lumen of the tubular member, the tubular implant having a delivery length when in a radially collapsed, delivery configuration within the delivery catheter, and a foreshortened length in a radially expanded, implanted configuration when released out of the delivery catheter, the foreshortened length shorter than the delivery length;

a pusher member slidably disposed in the delivery catheter and having a distal end coupled to a proximal end of the tubular implant, wherein the tubular implant is detachably coupled to the pusher member for delivery through and out the open distal end of the delivery catheter;

a second radiopaque marker located on the tubular implant, the second marker positioned such that when the delivery catheter is retracted relative to the tubular implant to a position where the first marker is positioned at the second marker, a last proximal portion of the tubular implant extending from the position of the second marker to a proximal end of the tubular implant has a determined deployed length in its radially expanded and foreshortened configuration in a range between 2 mm to 5 mm; and a re-sheath radiopaque marker located on the tubular implant such that, when the first marker moves along with the delivery catheter relative to the re-sheath marker upon withdrawing the delivery catheter from the tubular implant, the re-sheath marker indicates a proximal-most position to which the first marker can be withdrawn beyond which the delivery catheter cannot be advanced distally to re-sheath the tubular implant into the delivery catheter, wherein the second marker is located distally from the re-sheath marker along the implant delivery system, wherein the second marker is located longitudinally along the implant delivery system based on a determined cross-section of the body lumen at a target proximal landing location to provide for the determined deployed length of the last proximal portion of the tubular implant.

2. The implant delivery system of claim 1, wherein the tubular implant comprises a stent or a flow diverter.

3. The implant delivery system of claim 1, wherein the tubular implant is self-expanding.

4. A method for delivering a tubular implant to a target location in a body lumen, the tubular implant having a delivery length when in a radially collapsed, delivery configuration, and a foreshortened length shorter than the delivery length when in a radially expanded, implanted configuration, the method comprising:

inserting an implant delivery system comprising the tubular implant disposed in the radially collapsed, delivery configuration within a delivery catheter into the body lumen and advancing the implant delivery system until a distal end of the tubular implant is adjacent a target distal landing location for the distal end of the tubular implant; and withdrawing the catheter until a first radiopaque marker disposed on the distal end of the delivery catheter reaches a second radiopaque marker located on the tubular implant at which point there is a last proximal portion of the tubular implant remaining to be deployed from the delivery catheter, wherein the last proximal portion has a determined deployed length, the determined deployed length being a foreshortened length of the proximal portion in its radially expanded configuration corresponding to a determined cross-section of the body lumen at a target proximal landing location for the proximal portion of the tubular implant, wherein the implant delivery system further comprises a re-sheath radiopaque marker disposed on the tubular implant, wherein when the delivery catheter is withdrawn to the point that the first marker reaches the re-sheath marker, the re-sheath marker indicates a position of the proximally withdrawn delivery catheter at which the catheter cannot be advanced distally to re-sheath the tubular implant into the delivery catheter, wherein the second marker is located distally from the re-sheath marker along the implant delivery system, wherein the second marker is located longitudinally along the implant delivery system based on the determined cross-section of the body lumen at the target proximal landing location to provide for the determined deployed length of the last proximal portion of the tubular implant.

5. The method of claim 4, further comprising determining a cross-section of the body lumen at the target proximal landing location; and locating the first marker longitudinally along the implant delivery system based on the determined cross-section to provide for the determined deployed length.

6. The method of claim 5, wherein determining a cross-section of the body lumen at the target proximal landing location comprises determining an average diameter of the body lumen along a portion of the body lumen at the target proximal landing location.

7. The method of claim 4, further comprising determining a cross-section of the body lumen at the target proximal landing location; and determining the determined deployed length based on the determined cross-section.

8. The method of claim 7, wherein determining a cross-section of the body lumen at the target proximal landing location comprises determining an average diameter of the body lumen along a portion of the body lumen at the target proximal landing location.

9. The method of claim 4, further comprising identifying a position of the first marker within the body lumen at the point at which the delivery catheter is withdrawn such that the first marker reaches the second marker; and determining, based on the identified position of the first marker and the determined deployed length of the last proximal portion of the tubular implant remaining to be deployed from the delivery catheter, whether a proximal landing location of the proximal portion of the tubular implant is clinically desirable.

10. The method of claim 4, further comprising identifying a position of the first marker within the body lumen at the point at which delivery catheter is withdrawn such that the first marker reaches the second marker;

determining, based on the identified position of the first marker and the determined deployed length of the last proximal portion of the tubular implant remaining to be deployed from the delivery catheter, a proximal landing location of the proximal portion of the tubular implant is clinically undesirable; and advancing the delivery catheter distally to fully re-sheath the tubular implant within the delivery catheter.

11. The method of claim 10, further comprising repositioning the implant delivery system with tubular implant fully re-sheathed within delivery catheter to a new location.

12. The method of claim 11, further comprising with the implant delivery system in the new location, withdrawing the catheter until the first marker on the delivery catheter reaches the second marker located on the implant delivery system;

identifying a position of the first marker within the body lumen at the point at which delivery catheter is withdrawn such that the first marker reaches the second marker; and determining, based on the identified position of the first marker and the determined deployed length of the last proximal portion of the tubular implant remaining to be deployed from the delivery catheter, whether a proximal landing location of the proximal portion of the tubular implant is clinically desirable.

* * * * *